United States Patent
Kwon et al.

(10) Patent No.: US 11,945,779 B2
(45) Date of Patent: Apr. 2, 2024

(54) INHIBITORS OF CANCER METASTASIS THROUGH INHIBITING MIGRATION AND INVASION OF CANCER CELLS

(71) Applicant: VSpharmtech, Daegu (KR)

(72) Inventors: Byoung-Mog Kwon, Daejeon (KR); Dong Cho Han, Daejeon (KR); Yae Jin Yoon, Daejeon (KR); Yu Jin Lee, Daejeon (KR); Jiyoun Choi, Daejeon (KR); Sangku Lee, Daejeon (KR)

(73) Assignee: VSPHARMTECH, Daegu (KR)

( * ) Notice: Subject to any disclaimer, the term of this patent is extended or adjusted under 35 U.S.C. 154(b) by 744 days.

(21) Appl. No.: 17/052,865

(22) PCT Filed: May 2, 2019

(86) PCT No.: PCT/KR2019/005277
§ 371 (c)(1),
(2) Date: Nov. 4, 2020

(87) PCT Pub. No.: WO2019/212261
PCT Pub. Date: Nov. 7, 2019

(65) Prior Publication Data
US 2021/0246105 A1    Aug. 12, 2021

(30) Foreign Application Priority Data
May 4, 2018    (KR) .................. 10-2018-0051936

(51) Int. Cl.
A61K 31/445    (2006.01)
A23L 33/10    (2016.01)
A61K 45/06    (2006.01)
C07D 211/14    (2006.01)

(52) U.S. Cl.
CPC ............ *C07D 211/14* (2013.01); *A23L 33/10* (2016.08); *A61K 45/06* (2013.01)

(58) Field of Classification Search
CPC .................................................. A61K 31/445
USPC ........................................................ 514/317
See application file for complete search history.

(56) References Cited

U.S. PATENT DOCUMENTS

| 8,716,288 B2 | 5/2014 | Kwon et al. |
| 2010/0087455 A1 | 4/2010 | Gant |
| 2013/0245068 A1* | 9/2013 | Kwon ............ A61P 17/00 514/327 |

FOREIGN PATENT DOCUMENTS

| KR | 10-2012-0050918 A | 5/2012 |
| KR | 10-1323728 B1 | 10/2013 |
| KR | 10-2016-0041746 A | 4/2016 |
| WO | 2009-018280 A2 | 2/2009 |
| WO | 2009-094457 A2 | 7/2009 |

OTHER PUBLICATIONS

International Search Report dated Aug. 26, 2019 for corresponding international application No. PCT/KR2019/005277, citing above references.
Written Opinion issued for corresponding International Patent Application No. PCT/KR2019/005277 dated Aug. 26, 2019, citing the Foreign Patent Document No. 1.
Marina Bacac et al., "Metastatic Cancer Cell", Annual Review of Pathology: Mechanism of Disease, 2008, pp. 221-247, vol. 3, www.annualreviews.org, cited in the Specification.
Peter Friedl et al., "Tumour-Cell Invasion and Migration: Diversity and Escape Mechanisms", Nature Cancer Review, 2003, pp. 362-374, vol. 3, www.nature.com/reviews/cancer, cited in the Specification.
Aneta et al., "Migrastatics—Anti-metastatic and Anti-invasion Drugs: Promises and Challenges", Trends in Cancer, Jun. 2017, pp. 391-406, vol. 3, No. 6, cited in the Specification.
Stephane R. Gross, "Actin binding proteins—Their ups and downs in metastatic life", Cell Adhesion & Migration, Apr. 2013, pp. 199-213, vol. 7, Issue 2, www.landesbioscience.com, cited in the Specification.

* cited by examiner

*Primary Examiner* — Raymond J Henley, III
(74) *Attorney, Agent, or Firm* — Hauptman Ham, LLP

(57) ABSTRACT

The present invention relates to a pharmaceutical composition for preventing or treating cancer metastasis, a health functional food, and a method for preventing or treating cancer metastasis using the same, containing a novel compound for inhibiting migration and invasion of cancer cells or a pharmaceutically acceptable salt thereof as an active ingredient.

8 Claims, 15 Drawing Sheets

DLD-1 Cell Migration Inhibition by CG-608; IC$_{50}$ value: 200 nM

DMSO     200 nM     500 nM

Apc-1 Cell Migration Inhibition by CG-608; IC$_{50}$ value: 250 nM

DMSO     200 nM     500 nM

NUGC-3 Cell Migration Inhibition by CG-608; IC$_{50}$ value: 2 μM

DMSO     1 μM     5 μM

HCC827 Cell Migration Inhibition by CG-608; IC$_{50}$ value: 1.5 μM

DMSO     1 μM     5 μM

| Example | Code | Structure | IC$_{50}$ (μM) | Note |
|---|---|---|---|---|
| Control | CG601 (Benproperine) | 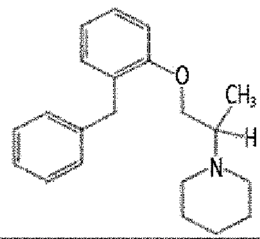 | 2 | Racemic mixture |
| Example 1 | CG609 | 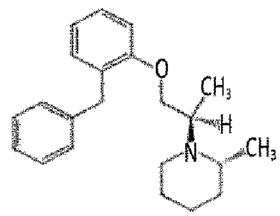 | 0.1 | S,R-form (2-Mthyl) |
| Example 2 | CG608 | 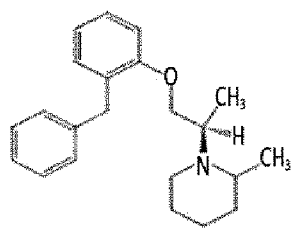 | 0.2 | S-form Racemic mixture (2-Methyl) |
| Example 3 | CG610 | 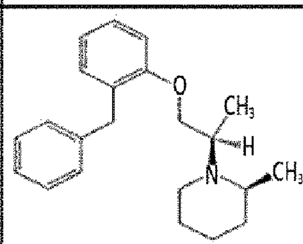 | 2 | S,S-form (2-Mthyl) |
| Example 4 | CG617 | 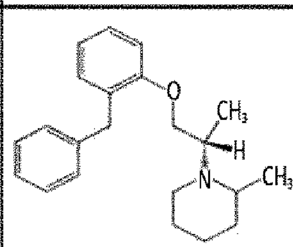 | 2 | R-form and Racemic mixture (2-Methyl) |
| Example 5 | CG618 | 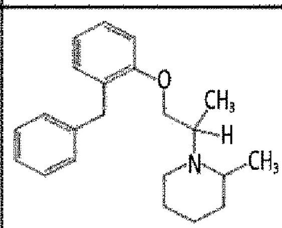 | 2 | Racemic mixture (2-Methyl) |

FIG. 12

| Example | Code | Structure | IC$_{50}$ (μM) | Note |
|---|---|---|---|---|
| Comparative Example 1 | CG605S | 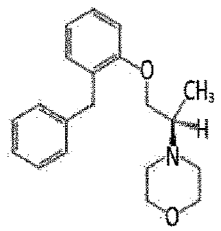 | 5 | S-form |
| Comparative Example 2 | CG606S | 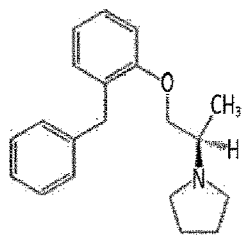 | 5 | S-form |
| Comparative Example 3 | CG607S | 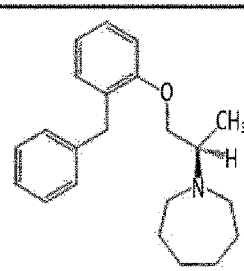 | 1.5 | S-form |
| Comparative Example 4 | CG611 | 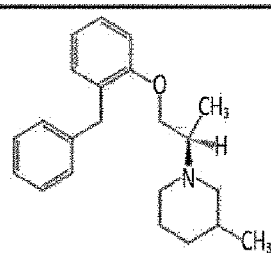 | 2 | S-form and Racemic mixture (3-Methyl) |
| Comparative Example 5 | CG612 | 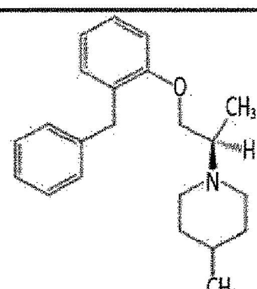 | 5 | S-form and Racemic mixture (4-Methyl) |

INHIBITORS OF CANCER METASTASIS THROUGH INHIBITING MIGRATION AND INVASION OF CANCER CELLS

CROSS-REFERENCE TO RELATED APPLICATION

The present application is a national stage filing under 35 U.S.C § 371 of PCT application number PCT/KR2019/005277 filed on May 2, 2019 which is based upon and claims the benefit of priority to Korean Patent Application No. 10-2018-0051936 filed on May 4, 2018, in the Korean Intellectual Property Office, which is incorporated herein in its entirety by reference.

TECHNICAL FIELD

The present invention relates to a benproperine derivative compound and more particularly, to a pharmaceutical composition for preventing or treating cancer metastasis and a health functional food for preventing or improving cancer metastasis, containing the compound or a pharmaceutically acceptable salt thereof as an active ingredient, and a method for preventing or treating cancer metastasis comprising treating the pharmaceutical composition to a subject.

BACKGROUND ART

According to data released by the American Cancer Society, 17% (7.6 million) of worldwide deaths in 2008 were due to cancer, and the number of deaths due to cancer is expected to surge to 9 million in 2015 and 11.4 million in 2030. Even in Korea, cancer remains the number one cause of death, and the number of deaths in 2016 was 280,827, a record high since relevant statistics have been compiled. The number one among 10 causes of death is cancer, and the number of deaths from cancer per 100,000 people is 153, and has been on the rise every year. As a result, the social costs are huge, and the need for the development of less toxic and more effective anti-cancer drugs has gradually increased. In addition, recently, due to the huge social costs of cancer, the development of drugs that can be treated at a low cost is required.

The biggest cause of a life-threatening cancer is the metastasis of cancer cells. Currently, there are surgical operations as a common method of treating cancer, but since cancer cells are metastasized to many other places besides the primary cancer site, a complete recovery through surgery may be expected only in the early stages.

Meanwhile, cancer metastasis, like cancer incidence, is made in a combination of various genes and factors involved in the migration and invasion of cancer cells (Marina Bacac and Ivan Stamenkovic. Annual Review of Pathology: Mechanism of Disease, 3, 221-247, 2008).

The migration of cancer cells plays an important role in cancer metastasis. For example, when cancer cells pass through the cell interstitial matrix (ECM) at the initial primary cancer site and then migrates to the blood vessels, or migrates out of the blood vessels at a secondary metastatic tissue, cancer metastasis is involved when vascular endothelial cells migrate from new blood vessels. The polarity of migrating cells is induced by signal receptors activated by a cell migration inductive material. In addition, the cell membrane at the front of the cell expands forward by way of the polymerization of actin, and the cell is attached to the cell interstitial matrix by integrin. At this time, a strong retraction force is formed between actin polymers by myosin bound to the actin polymer, and thus a strong retraction force is given to the entire cells. Accordingly, the direction of cell migration is determined by a difference in the adhesion between the front portion and the rear portion of the cell, and thus the cells migrate (Peter Friedl et al., Nature Cancer Review, 2003, 3: 362). Accordingly, a cell migration inhibitor inhibits migration of cancer cells to prevent the further spread of the metastasis, and an anti-cancer agent inducing the apoptosis of cancer cells may be administered while the migration is inhibited, so that it is considered as a realistic approach method to prolong the lives of cancer patients.

In accordance with these research trends, development of a cancer metastasis inhibitor using a substance for inhibiting migration of cancer cells, which is different from existing anti-cancer agents or cancer metastasis inhibitors targeting the growth of cancer cells, is claimed as a new alternative, which is called "Migrastatics" (Aneta Gandalovicova et al., Migrastatics-Anti-metastatic and Anti-invasion Drugs: Promises and Challenges, Trends in Cancer 3, 391, 2017).

A large number of factors are involved in the migration of cancer cells. Among them, protrusions called filopodia are formed, which are extended from fibrous tissues called lamellipodia around a cell skeleton or around the cell. These protrusion helps normal healthy cells to migrate within their tissues. However, in malignant cancers, the functions of normal healthy cells often become destructively excessive, resulting in excessive production of lamellipodia and filopodia. This phenomenon is inhibited to fundamentally prevent the migration of cancer cells (Stephane R. Gross, Actin binding proteins, Cell Adhesion & Migration 7, 199-213, 2013).

Meanwhile, the present inventors newly invented that a drug of benproperine used as an expectorant blocks migration of cancer cells and inhibits the development of neovascularization to effectively inhibit cancer metastasis (Korean Patent No. 10-1323728, U.S. Pat. No. 8,716,288, etc.).

However, since the drug inhibits the migration of cancer cells at a micromolar (mM) μM level, the development of drugs for inhibiting migration of cancer cells at a nanomolar (nM) level is required in accordance with a need for development of a highly active cancer metastasis inhibitor.

With this background, the present inventors made many efforts to develop a method capable of preventing or inhibiting cancer metastasis more effectively by inhibiting migration and invasion of cancer cells and as a result, developed a novel compound and confirmed that the compound has an excellent effect of inhibiting the migration and invasion of cancer cells at a nanomolar level, thus completing the present invention.

DISCLOSURE

Technical Problem

An object of the present invention is to provide a benproperine derivative compound, a compound having a structure of the following Chemical Formula 1, or a pharmaceutically acceptable salt thereof:

[Chemical Formula 1]

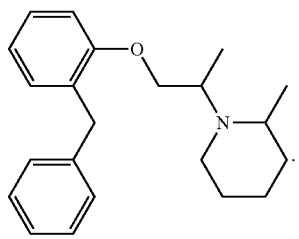

Another object of the present invention is to provide a pharmaceutical composition for preventing or treating cancer metastasis, containing the compound having the structure of Chemical Formula 1 or a pharmaceutically acceptable salt thereof as an active ingredient.

Yet another object of the present invention is to provide a health functional food for preventing or improving cancer metastasis, containing the compound having the structure of Chemical Formula 1 or a sitologically acceptable salt thereof as an active ingredient.

Still another object of the present invention is to provide a method for preventing or treating cancer metastasis, comprising administering, to a subject, a pharmaceutical composition containing the compound having the structure of Chemical Formula 1 or a pharmaceutically acceptable salt thereof as an active ingredient.

Technical Solution

Specifically, the present invention will be described as follows. Meanwhile, each description and embodiment disclosed in the present invention can also be applied to each of the other descriptions and embodiments. That is, all combinations of the various components disclosed in the present invention belong to the scope of the present invention. In addition, the specific description described below may not limit the scope of the present invention.

In order to achieve the objects of the present invention, an aspect of the present invention provides a compound having a structure of the following Chemical Formula 1 or a pharmaceutically acceptable salt thereof, as a benproperine derivative compound:

[Chemical Formula 1]

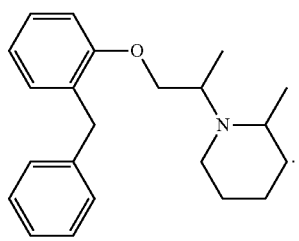

The compound of the present invention has two stereocenters or chiral centers, that exist within a single molecule as follows:

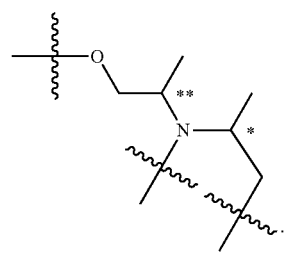 [SMILES: *CC(C)N(*)C(C)CO*]

Therefore, even if not otherwise indicated, the compound of Chemical Formula 1 contains all stereoisomers such as an (R,R)-form, an (R,S)-form, an (S,R)-form, and an (S,S)-form, that may be derived from the compound, without limitation. Further, a racemic mixture is also included in the scope of the present invention, in which enantiomers such as an (R,R)-form and an (S,S)-form, and an (R,S)-form and an (S,R)-form, and diastereomers such as an (R,R)-form and an (R,S)-form, and an (S,R)-form and an (S,S)-form are mixed with each other at a 1:1 ratio. Furthermore, either an (R)-form or an (S)-form with respect to one stereocenter, a compound in which the (R)-form and the (S)-form are mixed with respect to the other stereocenter, and a mixture in which the (R)-form and the (S)-form are mixed, that is, the (R,R)-form, the (R,S)-form, the (S,R)-form, and the (S,S)-form are randomly mixed with respect to the two stereocenters, are included in the scope of the present invention.

These isomers may be represented by the following Chemical Formulas.

[Chemical Formula 2]

CG-608

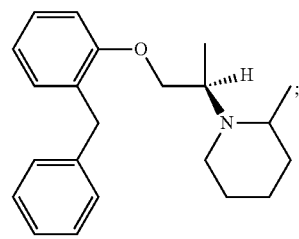

[Chemical Formula 3]

CG-609

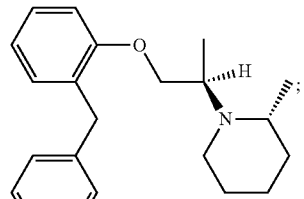

[Chemical Formula 4]

CG-610

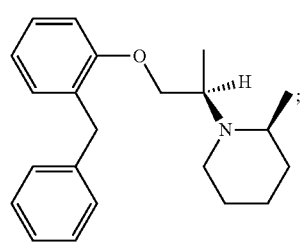

[Chemical Formula 5]

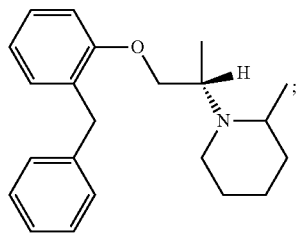

CG-617

In the Chemical Formulas, among the bonds located at the stereocenter, a bond indicated by a normal solid line means a form of a mixture in which all possible stereo-bonds exist.

The number written on the right side of Chemical Formula is an identification number arbitrarily given to facilitate the identification of the synthesized isomers.

Further, a mixture in which all stereo structures formed in each stereocenter, for example, the (R,R)-form, the (R,S)-form, the (S,R)-form, and the (S,S)-form, are randomly mixed is called CG-618. According to the bonds defined in the Chemical Formulas above, CG-618 may be marked the same as in Chemical Formula 1 above, but is not separately marked to prevent confusion.

Another aspect of the present invention provides a method for preparing the compound of Chemical Formula 1 or a pharmaceutically acceptable salt thereof, comprising reacting 1-(2-benzylphenoxy)propan-2-yl 4-methylbenzenesulfonate with 2-methylpiperidine.

Each reagent used in the preparation method of the present invention may be used by purchasing commercially available compounds, and may be used by preparing compounds prepared according to known methods.

For example, in the preparation method of the present invention, 1-(2-benzylphenoxy)propan-2-yl 4-methylbenzenesulfonate may be prepared by reacting 1-(2-benzylphenoxy)propan-2-ol with 4-methylbenzene-1-sulfonyl chloride, but is not limited thereto.

Furthermore, 1-(2-benzylphenoxy)propan-2-ol may be prepared by reacting 2-benzylphenol with propylene oxide, but is not limited thereto.

At this time, among the compounds used, 2-methyl piperidine, propylene oxide, or both may be used by selecting the pure (R)-form or (S)-form, or a racemate thereof to selectively synthesize various stereoisomers, diastereomers, and/or racemates of the compound of Chemical Formula 1.

In a specific embodiment of the present invention, the compound represented by Chemical Formula 1 is synthesized from propylene oxide and 2-benzyl phenol, in which any one of (R)-(+)-propylene oxide, (S)-(−)-propylene oxide, and a racemic mixture thereof as the propylene oxide, and any one of (R)-2-methyl piperidine, (S)-2-methyl piperidine and a racemic mixture thereof as 2-methyl piperidine are combined and used as a reactant to synthesize a total of 9 types of structural isomers, diastereomers, or racemic mixtures.

For example, in Example 1, an R,R-form compound called the CG-609 was synthesized using (R)-(+)-propylene oxide and (R)-2-methyl piperidine, and in Example 9, an R,R-form, an R-S-form, an S-form, and an S-S-form were evenly mixed using propylene oxide and 2-methyl piperidine provided as a racemic mixture to obtain a random racemic mixture called CG-618.

For example, in the step of reacting 1-(2-benzylphenoxy)propan-2-yl 4-methylbenzenesulfonate with 2-methyl piperidine, 1-(2-benzylphenoxy)propan-2-yl 4-methylbenzenesulfonate was dissolved in 4 to 8 molar equivalents of 2-methyl piperidine and then refluxed at 100° C. to 150° C. for 2 to 10 hours.

After the reaction, steps of further stirring at room temperature of 15° C. to 35° C. for 6 to 24 hours, removing a large amount of piperidine by diluting the reaction mixture and then concentrating the diluted mixture under reduced pressure, extracting the reaction solution after increasing pH by adding a base, drying, filtering, concentrating, and/or purifying may be additionally performed, but the steps are not limited thereto. The additional steps may be performed by using a general method used in the art without limitation.

The present invention may be provided in the form of the compound represented by Chemical Formula 1 or a pharmaceutically acceptable salt thereof. In this case, the pharmaceutically acceptable salt means a formulation that does not impair the biological activity and properties of a compound to be administered.

The term "pharmaceutically acceptable salt" of the present invention refers to any organic or inorganic addition salt of the compound at a concentration that is relatively non-toxic and has a harmless effective effect on a patient in which side effects caused by the salt do not degrade the beneficial effect of the compound represented by Chemical Formula 1.

The pharmaceutically acceptable salt may contain, for example, a non-toxic acid addition salt formed by free acids containing pharmaceutically acceptable anions. The acid addition salt is prepared by a general method, for example, by dissolving the compound represented by Chemical Formula 1, stereoisomers thereof, or mixtures thereof in a large amount of an aqueous acid solution and precipitating the salt using a water-miscible organic solvent, for example, methanol, ethanol, acetone, or acetonitrile. Alternately, the acid addition salt may be prepared by heating the compound represented by Chemical Formula 1, stereoisomers thereof, or mixtures thereof, and an acid or alcohol (e.g., glycol monomethyl ether) in water and then evaporating and dying the mixture or suction-filtering the precipitated salt. For the free acid, an acid addition salt formed by, for example, an inorganic acid such as hydrochloric acid, sulfuric acid, nitric acid, phosphoric acid, hydrobromic acid, and hydroiodic acid, an organic carbonic acid such as tartaric acid, formic acid, citric acid, acetic acid, trichloroacetic acid, trifluoroacetic acid, gluconic acid, benzoic acid, lactic acid, fumaric acid, maleic acid, and salicylic acid, and a sulfonic acid such as methane sulfonic acid, ethanol sulfonic acid, benzene sulfonic acid, and p-toluene sulfonic acid may be included, but the free acid is not limited thereto. The pharmaceutically acceptable carboxylic acid salt may contain a metallic salt or an alkali earth metal salt formed by lithium, sodium, potassium, calcium, magnesium, and the like, an amino acid salt such as lysine, arginine, and guanidine, and an organic salt such as dicclohexylamine, N-methyl-D-glucamine, tris(hydroxymethyl)methylamine, diethanolamine, choline, and triethylamine.

Further, the pharmaceutically acceptable salt may contain a pharmaceutically acceptable metal salt prepared using a base. The alkali metal salt or the alkaline earth metal salt may be obtained by dissolving the compound in a large amount of an alkali metal hydroxide or alkaline earth metal hydroxide solution, filtering a non-dissolved compound salt, and then evaporating and drying a filtrate. In this case, the metal salt is pharmaceutically suitable to prepare, particularly, sodium, potassium, or calcium salts, but is not limited thereto. Further, the silver salt corresponding thereto may be obtained by reacting alkali metal or alkaline earth metal salts with an appropriate silver salt (e.g., silver nitrate).

The pharmaceutically acceptable salt may include all organic or inorganic addition salts of the compound represented by Chemical Formula 1, and the stereoisomers thereof or the mixtures thereof, in addition to the salts described above.

Yet another aspect of the present invention provides a pharmaceutical composition for preventing or treating cancer metastasis, containing the compound having the structure of Chemical Formula 1 or a pharmaceutically acceptable salt thereof as an active ingredient.

The compound having the structure of Chemical Formula 1 or the pharmaceutically acceptable salt thereof is as described above.

In an embodiment of the present invention, it was confirmed that CG-609, corresponding to a representative example of a chiral compound, effectively inhibited the migration of colon cancer cells, pancreatic cancer cells, melanoma cells, lung cancer cells, prostate cancer cells, and stomach cancer cells, which were representative cancer cells (FIG. 3). It was confirmed that CG-609 had activity that inhibited the migration of colon cancer cells, pancreatic cancer cells, lung cancer cells, and skin cancer cells by 50% or more at a nanomolar level, and inhibited the migration of prostate cancer cells, and stomach cancer cells by 50% or more at a concentration of several micromoles (FIGS. 4A and 4B).

Further, it was confirmed that CG-608 had activity that inhibited the migration of colon cancer cells and pancreatic cancer cells by 50% or more at a nanomolar level, and inhibited the migration of stomach cancer cells and prostate cancer cells by 50% or more at a concentration of several micromoles (FIG. 5).

Further, it was confirmed that CG-618 had activity that inhibited the migration of colon cancer cells, pancreatic cancer cells, and lung cancer cells by 50% or more at a nano mole level, and inhibited the migration of skin cancer cells and prostate cancer cells by 50% or more at a concentration of several micromoles (FIGS. 6A and 6B). In particular, it was shown that CG-618 had effective cancer cell migration inhibitory activity even at a concentration which was three times lower than that of a known benproperine drug, and this is a result of suggesting that better cancer metastasis inhibitory drugs may be developed at a lower cost of production in future industrialization.

In another embodiment of the present invention, it was confirmed that CG-609 and CG-618 had no effect on the migration and growth of normal cells, and a possibility of development of less toxic cancer metastasis inhibitory drugs was directly verified (FIG. 2).

In addition, in another embodiment of the present invention, it was confirmed that CG-609 and CG-618 did not affect the growth of cancer cells and very strongly inhibited invasion of cancer cells at low concentrations (FIG. 8). In addition, it was confirmed that CG-618 inhibited a process of forming protrusions called lamellipodia and filopodia, one of the important processes for cancer cell migration at a cell level, and had no effect on normal cells (FIG. 9). In addition, as a result of confirming an effect of CG-618 on the migration of single cells by using real-time cell migration imaging and analysis equipment, it was confirmed that CG-618 strongly inhibited the migration of cancer cells, but increased the migration of normal cells (FIG. 7). Further, as a result of confirming an effect of the drug on the migration of single cells using real-time cell migration imaging and analysis equipment, HoloMonitor M4 (Phase Holographic Imaging), it was confirmed that the migration of cells treated with CG-618 was significantly reduced, but the migration of normal cells was increased (FIG. 7).

Furthermore, in another embodiment of the present invention, it was confirmed that CG-609 very strongly inhibited cancer metastasis by oral administration at 5 mg/kg or 10 mg/kg in an animal model for evaluating cancer metastasis efficacy in a human-derived colon cancer luminescence cell line (HCT-116 luciferase) (FIGS. 10A and 10B). Accordingly, the pharmaceutical composition of the present invention may be used to prevent or treat various cancer metastasis by not only inhibiting the migration or invasion of cancer cells but also effectively inhibiting cancer metastasis in a cancer metastasis animal model.

Further, in a specific embodiment of the present invention, the compound of Chemical Formula 1, as a compound of the Comparative Example, has a similar chemical structure to benproperine, a known material used as a control compound, and GC-605S, a derivative that introduces oxygen, a hetero element in a piperidine ring, GC-606S and GC-607S, derivatives that reduce or extend the piperidine ring to 5-membered or 6-membered rings, and GC-611 and GC-612, derivatives that modify a position of a methyl substituent on the piperidine ring, were synthesized, and the $IC_{50}$ values for the migration of colon cancer cells, DLD-1, were calculated and compared. As a result, it was confirmed that these compounds exhibited an equivalent or lower cancer cell migration inhibitory effect compared to the control group, benproperine, indicating that even with similar chemical structures, the cancer treatment effects exhibited by these compounds may be completely different from each other.

The term "cancer" of the present invention means a condition in which a problem in a regulatory function of normal cell division, differentiation, and apoptosis occurs, and thus the cells abnormally excessively proliferate to and invade surrounding tissues and organs to form a cancer tissue, and an existing structure is broken or modified. The cancers are divided into primary cancers, existing in an area of occurrence, and metastatic cancers, diffused from the area of occurrence to other organs of the body.

The cancer may refer to, for example, colon cancer, pancreatic cancer, stomach cancer, liver cancer, breast cancer, cervical cancer, thyroid cancer, parathyroid cancer, lung cancer, prostate cancer, gallbladder cancer, biliary tract cancer, non-Hodgkin's lymphoma, Hodgkin's lymphoma, blood cancer, bladder cancer, kidney cancer, ovarian cancer, melanoma, colon cancer, bone cancer, skin cancer, head cancer, uterine cancer, rectal cancer, brain tumor, anal cancer, paraplegic cancer, endometrial cancer, vaginal cancer, mucinoma, esophageal cancer, small intestine cancer, endocrine gland cancer, adrenal cancer, soft tissue sarcoma, urethral cancer, penis cancer, ureteric cancer, kidney cell carcinoma, kidney pelvic cancer, CNS (central nervous system) tumor, primary CNS lymphoma, spinal cord tumor, brainstem glioma, or pituitary adenoma, but is not limited thereto. The melanoma may occur in the skin, eye, mucous membrane, or central nervous system.

The migration of cancel cells is caused by the spread of cancer cells through blood circulation or lymphatic circulation and usually transfer cancer cells to another organ through blood circulation to then form a new tumor.

The invasion of cancer cells means that the cancer cells are proliferated by penetrating the surrounding tissue at the site where the cancer first occurred, and the cancer cells migrate directly to and penetrate the neighboring tissues.

The term "prevention" used in the present invention may mean all actions that inhibit or delay the occurrence, growth, proliferation, migration, and invasion of cancer cells by administering the compound having the structure of Chemical Formula 1 according to the present invention or the pharmaceutically acceptable salt thereof to a subject.

The term "treatment" used in the present invention may mean all actions which improve or benefit the symptoms of cancer by administering the composition to a subject suspected of having cancer.

The pharmaceutical composition of the present invention may additionally include pharmaceutically acceptable carriers, excipients, or diluents.

The term "pharmaceutically acceptable carrier" used in the present invention may refer to a carrier or a diluent which does not inhibit biological activity and properties of a compound to be injected without stimulating organisms. The type of carrier usable in the present invention is not particularly limited and may be used in any carriers which are commonly used in the art and pharmaceutically acceptable. Non-limitative examples of the carrier may include a saline solution, sterile water, Ringer's solution, a buffer saline solution, an albumin injection solution, a dextrose solution, a maltodextrin solution, glycerol, and ethanol. These may be used alone or in combination of two or more kinds. In addition, other common additives, such as antioxidants, buffer solutions, and/or fungicides, may be added and used if necessary. The pharmaceutical composition may be formulated in a unit dose form or formulated to be injected in a multi-dose container. For example, the pharmaceutical composition may have any formulation selected from the group consisting of tablets, pills, powders, granules, capsules, suspensions, liquids for internal use, emulsions, syrups, sterile aqueous solutions, non-aqueous solvents, suspensions, emulsions, lyophilized formulations, and suppositories, and may be various oral or parenteral formulations. When the composition is formulated, the formulation may be prepared by using a diluent or an excipient, such as a filler, an extender, a binder, a wetting agent, a disintegrating agent, and a surfactant, which are generally used. A solid formulation for oral administration includes a tablet, a pill, a powder, a granule, a capsule, and the like, and the solid formulation may be prepared by mixing at least one excipient, for example, starch, calcium carbonate, sucrose or lactose, gelatin, and the like with at least one compound. Further, a lubricant such as magnesium stearate and talc may also be used in addition to the simple excipient. A liquid formulation for oral administration may correspond to a suspension, an internally applied solution, an emulsion, a syrup, and the like, and may include various excipients, for example, a wetting agent, a sweetener, an aromatic agent, a preserving agent, and the like in addition to water and liquid paraffin, which are commonly used as simple diluents. A formulation for parenteral administration includes a sterile aqueous solution, a non-aqueous solution, a suspension, an emulsion, and a lyophilizing agent, and a suppository. As the non-aqueous solution and the suspension, propylene glycol, polyethylene glycol, vegetable oil such as olive oil, injectable ester such as ethyl oleate, and the like may be used. As a base matter of the suppository, witepsol, macrogol, tween 61, cacao butter, laurinum, glycerogelatin, and the like may be used.

The pharmaceutical composition of the present invention may be used as a single agent. In addition, the pharmaceutical composition may be prepared and used as a complex agent by further including at least one kind of anti-cancer agent. The anti-cancer agent may be at least one selected from the group consisting of DNA alkylating agents, anti-cancer antibiotics, and plant alkaloids, but is not limited thereto. For example, the anti-cancer agent may be at least one selected from the group consisting of mechloethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin, C-bleomycin; vincristine, vinblastine, paclitaxel, docetaxel, etoposide, teniposide, topotecan, and iridotecan.

Yet another aspect of the present invention provides a health functional food for preventing or improving cancer metastasis, containing the compound having the structure of Chemical Formula 1, stereoisomers thereof, a mixture thereof, or a sitologically acceptable salt thereof as an active ingredient.

The compound having the structure of Chemical Formula 1 is as described above.

The term "health functional food" in the present invention refers to food prepared and processed in the form of tablets, capsules, powders, granules, liquids, and pills using raw materials or ingredients having functionalities useful to the human body. Here, the functionality refers to the adjustment of nutrients to the structure and function of the human body or to obtainment of effects useful for health applications such as physiological action. The health functional food of the present invention may be prepared by methods which are commonly used in the art and may be prepared by adding raw materials and ingredients which are commonly added in the art in preparation. In addition, unlike general drugs, the food may be used as raw materials to have an advantage without side effects which may be caused by long-term use of drugs and have excellent portability.

The mixed amount of the active ingredient may be suitably determined according to the purpose of use (prevention, health, or therapeutic treatment). In general, the compound of the present invention is added in an amount of 1 wt % to 10 wt %, preferably 5 wt % to 10 wt % of the raw material composition in the preparation of food. However, in the case of long-term ingestion for the purpose of health and hygiene or health regulation, the amount may be used below the above range.

The health functional food of the present invention may be used for prevention or improvement of cancer metastasis.

Still another aspect of the present invention provides a method for preventing or treating cancer metastasis, comprising administering, to a subject, a pharmaceutical composition containing the compound having the structure of Chemical Formula 1, stereoisomers thereof, a mixture thereof, or a pharmaceutically acceptable salt thereof as an active ingredient.

The pharmaceutical composition refers to a pharmaceutical composition for preventing or treating cancer, containing the compound having the structure of Chemical Formula 1, stereoisomers thereof, a mixture thereof, or a pharmaceutically acceptable salt thereof as an active ingredient.

The term "subject" used in the present invention may refer to all animals except for a human or including humans, that have cancer or are likely to develop cancer. These animals may be mammals such as cattle, horses, sheep, pigs, goats, camels, antelope, dogs, and cats that require treatment for similar symptoms as well as humans, but are not limited thereto.

The method for prevention or treatment of the present invention may specifically include administering the composition in an effective dose to a subject that has developed cancer or is at risk of developing cancer.

The "effective dose" is a pharmaceutically effective dose and refers to an amount which is sufficient to treat the diseases at a reasonable benefit/risk ratio applicable to medical treatment, and an effective dose level may be determined according to elements including a kind of subject, the severity, age, gender, activity of a drug, sensitivity to a drug, a time of administration, a route of administration, and an emission rate, duration of treatment, and simultaneously used drugs, and other elements well-known in the medical field. For example, a dose of 0.01 mg/kg to 100 mg/kg, preferably 0.5 mg/kg to 10 mg/kg, and more preferably 1 mg/kg to 5 mg/kg may be administered once to several times a day. The composition of the present invention may be administered as an individual therapeutic agent or administered in combination with other therapeutic agents, and sequentially or simultaneously administered with therapeutic agents in the related art. In addition, the composition of the present invention may be administered in alone or in a multiple does form.

It is important to administer an amount capable of obtaining a maximum effect with a minimal amount without side effects by considering all of the elements and the amount may be easily determined by those skilled in the art. A preferable dose of the composition of the present invention varies according to a patient's condition and body weight, disease severity, drug forms, and administration route and duration. The administration may be performed once a day or several times a day. Further, it is also preferable for the dose to be differently applied according to various factors, including a drug used with or simultaneously used with a specific composition, and similar factors that are well known in the field of medicine. The composition may be administered by various routes to various mammals, such as rats, livestock, and humans, and the method of administration includes any general method in the art without limitation, but oral administration is preferable.

The "administration" used in the present invention means introducing the pharmaceutical composition of the present invention to a patient by any suitable method, and the composition of the present invention may be orally or parenterally administered through various routes which may reach a target tissue. The administration method of the pharmaceutical composition of the present invention is not particularly limited and may follow methods which are commonly used in the art. As a non-limitative example of the administration method, the composition may be administered either orally or parenterally. The pharmaceutical composition according to the present invention may be prepared in various formulations depending on a desired administration method.

The frequency of administration of the composition of the present invention is not particularly limited, but the composition may be administered once a day or several times a day by dividing the dose.

In an embodiment of the present invention, it was confirmed that CG-608, CG-609, and CG-618 had activity of inhibiting the migration of colon cancer cells, pancreatic cancer cells, skin cancer cells, and lung cancer cells which are representative cancer cell lines. In particular, a result was confirmed suggesting that CG-608, CG-609, and CG-618 had effective activity of inhibiting cancer metastasis even at a concentration 10 times or more lower than benproperine, which is the structural nucleus of the drug (FIGS. 4A, 4B, 5, 6A, 6B, and 8). Further, in another embodiment of the present invention, it was confirmed that CG-609 inhibited cancer metastasis by 50% or more even at a dose (5 mg/kg) 10 times lower than that of benproperine (50 mg/kg) in an animal experiment (FIGS. 10A and 10B). Therefore, the pharmaceutical composition of the present invention may be usefully used to prevent or treat various cancers in animals including humans by not only inhibiting the migration or invasion of cancer cells but also inhibiting cancer metastasis in an animal experiment.

The terms of the present invention, that is, CG-608, CG-609. CG-618, cancers, prevention, or improvement are described above.

Still another aspect of the present invention provides use of the compound having the structure of Chemical Formula 1 or a pharmaceutically acceptable salt thereof in preparation of an anticancer treatment agent.

Still another aspect of the present invention provides use of the compound having the structure of Chemical Formula 1 or a pharmaceutically acceptable salt thereof in preparation of an agent for preventing or treating migration of cancer.

Still another aspect of the present invention provides use of the compound having the structure of Chemical Formula 1 or a pharmaceutically acceptable salt thereof for treating cancer.

Advantageous Effects

A novel compound of the present invention or a pharmaceutically acceptable salt thereof has an excellent effect of inhibiting migration and invasion of various cancer cells, and in particular, has an excellent effect of inhibiting cancer metastasis compared with benproperine known in the art, and thus may be usefully used as the pharmaceutical composition for preventing or treating cancer metastasis, and as a method for preventing or treating cancer metastasis using the same.

DESCRIPTION OF DRAWINGS

FIG. 12 is a diagram illustrating $IC_{50}$ values for migration of a colon cancer cell line DLD-1 in Structural Formulas of compounds of Comparative Examples 1 to 5 and compounds thereof.

MODE FOR INVENTION

Figure 1:
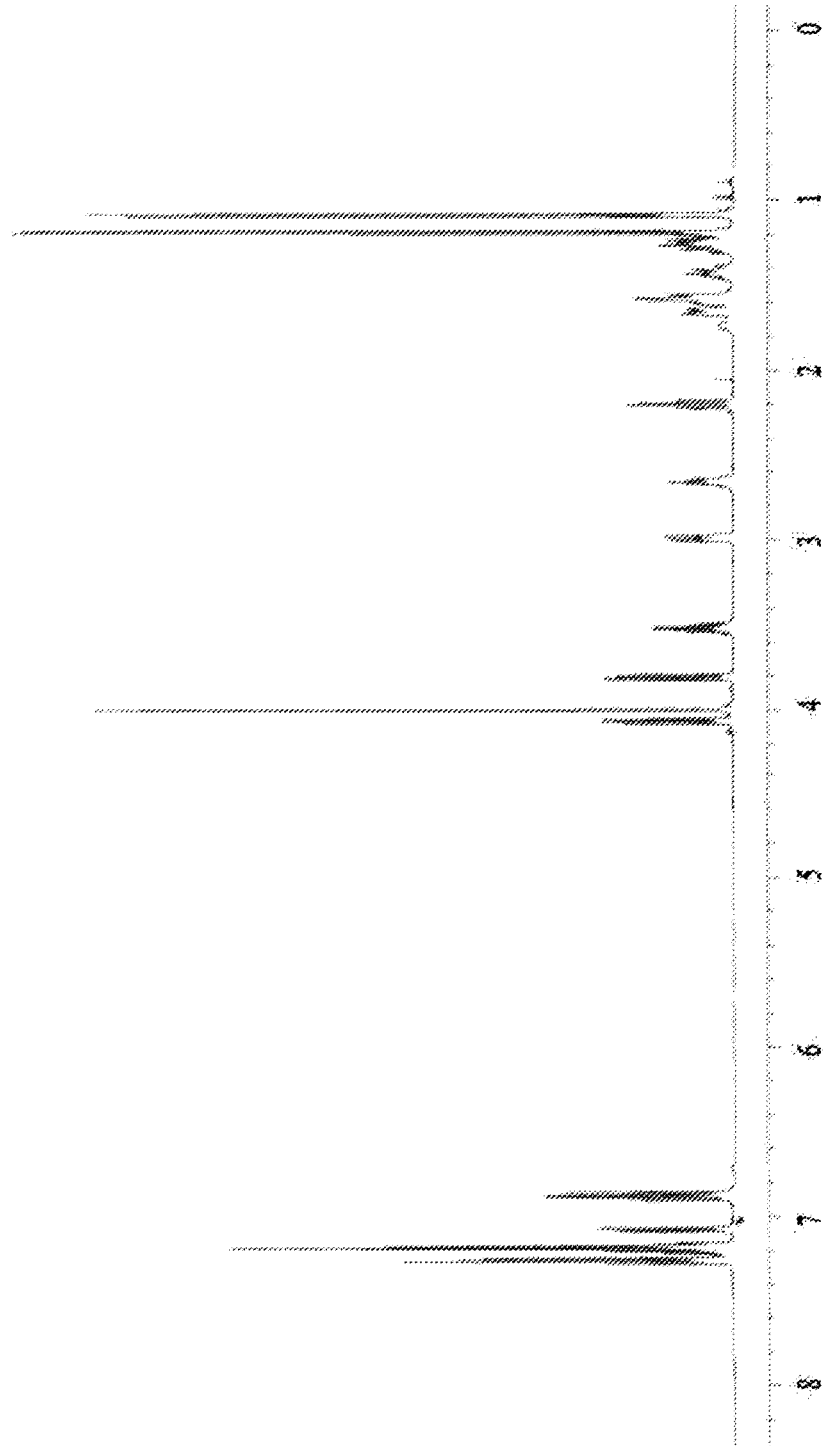
FIG. 1 is a diagram illustrating a $^1$H-NMR spectrum of CG-609.

Hereinafter, configurations and effects of the present invention will be described in more detail through Examples. The following Examples are only provided for illustrating the present invention, and the scope of the present invention is not limited by the following Examples.

Example 1: Synthesis of CG-609

As a representative example of a chiral compound, a compound CG-609 was synthesized by the same method as the following Reaction Formula 1:

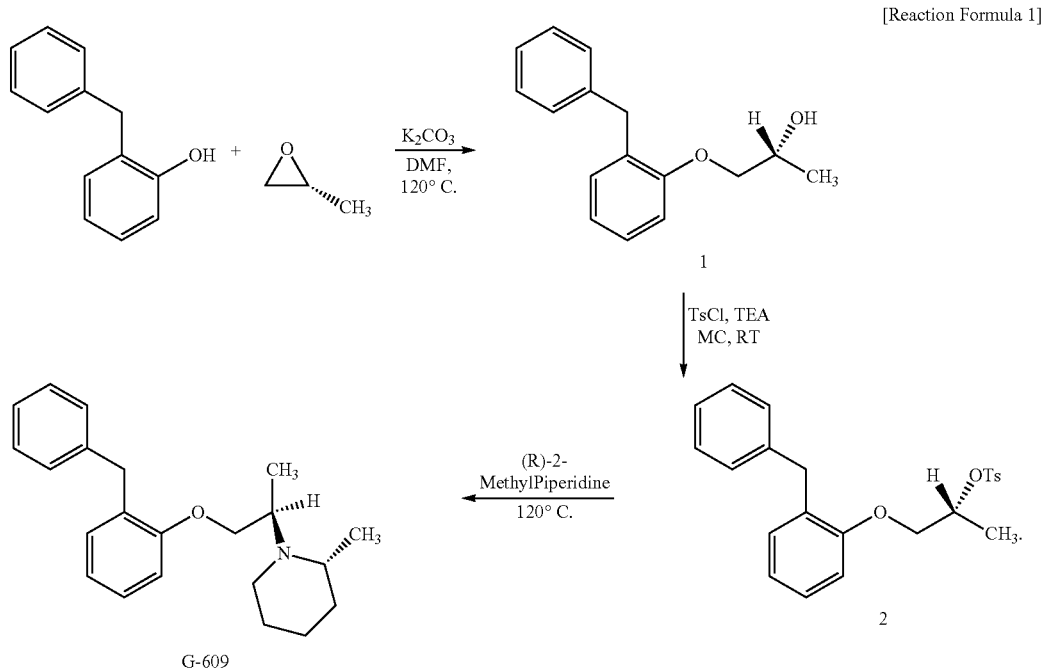

[Reaction Formula 1]

(1) Synthesis of Compound 1 [(R)-1-(2-benzylphenoxy)propan-2-ol]

$K_2CO_3$ (1.2 g, 8.68 mmol) was added to N,N-dimethylformamide (DMF, 0.85 M, 5 mL) and stirred. After 5 minutes, 400 mg (2.17 mmol) of 2-benzylphenol was added at room temperature. After 30 minutes, 0.9 mL (13.91 mmol) of (R)-(+)-propylene oxide was rapidly added using a syringe. Thereafter, the mixture was heated at 120° C. and stirred for 17 hours. After the mixture was cooled to room temperature, the reaction was completed by adding water, and then the mixture was extracted three times using ethyl acetate and water. Thereafter, an organic layer was washed with water three times and then washed with salt water once more. The organic layer was dried using $MgS_4$, filtered, and then concentrated under reduced pressure. The concentrate was purified using column chromatography (EA:Hex=1:9) to obtain Compound 1 [(R)-1-(2-benzylphenoxy)propan-2-ol, 970 mg, 92.4%, bright yellow oil]. The H-NMR analysis result of Compound 1 is as follows:

$^1$H-NMR (300 MHz, $CDCl_3$) δ 7.30-7.15 (m, 7H), 6.94 (td, J=7.2, 1.2 Hz, 14), 6.81 (d, J=8.7 Hz, 11H), 4.06-4.03 (m, 1H), 4.00 (d, J=5.4 Hz, 2H), 3.89 (dd, J=9.3, 3.0 Hz, 1), 3.66 (dd, J=9.3, 7.8 Hz, 1H), 1.78 (d. J=3.6 Hz, 1H), 1.18 (d, J=6.0 Hz, 3H);

$^{13}$C-NMR (75 MHz, CDCl$_3$) δ 156.34, 141.22, 131.00, 129.18, 128.45, 128.26, 127.77, 126.01, 120.81, 111.20, 78.08, 66.10, 37.10, 18.36.

(2) Synthesis of Compound 2 [(R)-1-(2-benzylphenoxy)propan-2-yl 4-methylbenzenesulfonate]

Compound 1 (400 mg, 1.73 mmol) was dissolved in methylene chloride (MC, 0.25M, 7 mL). Thereafter, 0.59 mL (4.21 mmol) of triethylamine (TEA), 106 mg (0.87 mmol) of p-dimethylanimopyridine (DMAP), and 410 mg (2.25 mmol) of p-toluenesulfonyl chloride (TsCl) were sequentially added and then stirred at room temperature for 16 hours. Thereafter, the reaction was completed by adding water and the mixture was extracted three times using methylene chloride (MC) and water. Thereafter, the MC layer was washed with water two times and then washed with salt water once more. The MC layer was dried using MgSO$_4$, filtered, and then concentrated under reduced pressure. The concentrate was purified using column chromatography (EA:Hex=1:9) to obtain Compound 2 [(R)-1-(2-benzylphenoxy)propan-2-yl 4-methylbenzenesulfonate, 505 mg, 73.5%, brown oil]. The $^1$H-NMR analysis result of Compound 2 is as follows:

$[α]^{25}_D$+78.7° (c 1, EtOH);
$^1$H-NMR (300 MHz) δ 7.78 (d, 2H, J=8.1 Hz), 7.27-7.11 (m, 8H), 7.03 (dd, J=7.2, 1.2 Hz, 1H), 6.88 (t. J=7.2 Hz, 1H), 6.70 (d, 1H, J=8.7 Hz), 4.87 (m, 1H), 4.01 (dd, 1H, J=10.5, 5.4 Hz), 3.89 (dd, 1H, J=10.5, 5.4 Hz), 3.80 (s, 2H), 2.37 (s, 3H), 1.34 (d, 3H, J=6.9 Hz);
$^{13}$C-NMR (75 MHz) δ 155.6, 144.7, 140.7, 134.0, 130.5, 129.9, 129.7, 128.9, 128.2, 127.7, 127.3, 125.8, 121.1, 111.1, 76.9, 69.7, 35.7, 21.5, 17.8.

(3) Synthesis of CG-609

Compound 2 (435 mg, 1.09 mmol) was dissolved in (R)-2-methylpiperidine (0.65 mL, 6.59 mmol) and then refluxed at 120° C. for 5 hours. Thereafter, the mixture was stirred at room temperature for 12 hours. The stirred reaction mixture was diluted with methanol and concentrated under reduced pressure (removing a large amount of piperidine). Then, 43 mL of 1 M sodium hydroxide (NaOH) was added to form a basic condition, and then extracted three times using ether and water. Then, the ether layer was washed with salt water. The ether layer was dried using MgSO$_4$, filtered, and then concentrated under reduced pressure. The concentrate was purified using column chromatography (EA: Hex=1:1) to obtain CG-609 ((S)-1-((R)-1-(2-benzylphenoxy)propan-2-yl)-2-methylpiperidine, 201 mg, 55.2%, brown oil). The $^1$H-NMR analysis result of CG-609 is as follows:

$[α]^{25}_D$-121.8° (c1, EtOH);
$^1$H-NMR (300 MHz) δ 7.26-7.13 (m, 7H), 7.05 (m, 2H), 4.05 (dd, 1H, J=9.5, 5.0 Hz), 4.98 (s, 2H), 3.78 (dd, 1H, J=9.0, 5.5 Hz), 3.51 (m, 1H), 2.97 (m, 1H), 2.64 (m, 1H), 2.18 (m, 1H), 1.15 (m, 3H), 1.42 (m, 1H), 1.23 (m, 2H), 1.17 (d, 3H, J 7.0 Hz), 1.07 (d, 3H, J=5.5 Hz);
$^{13}$C-NMR (75 MHz) δ 156.7, 140.9, 130.5, 129.3, 128.7, 128.1, 127.3, 125.7, 120.3, 110.8, 67.5, 54.7, 51.7, 45.5, 36.1, 35.7, 26.7, 24.5, 19.9, 16.7.

$^1$H-NMR data of the CG-609 synthesized above was illustrated in FIG. 1.

Example 2: Synthesis of CG-608

CG-608 (1-((S)-1-(2-benzylphenoxy)propan-2-yl)-2-methylpiperidine) was synthesized in the same manner as the synthesis method of CG-609, and there was a difference in that 2-methyl piperidine instead of (R)-2-methyl piperidine was used as a reaction material.

Example 3: Synthesis of CG-610

CG-610 ((S)-1-((S)-1-(2-benzylphenoxy)propan-2-yl)-2-methylpiperidine) was synthesized in the same manner as the synthesis method of CG-609, and there was a difference in that (S)-2-methyl piperidine instead of (R)-2-methyl piperidine was used as a reaction material.

Example 4: Synthesis of CG-617

CG-617 (1-((R)-1-(2-benzylphenoxy)propan-2-yl)-2-methylpiperidine) was synthesized in the same manner as the synthesis method of CG-609, and there was a difference in that (S)-(−)-propylene oxide instead of (R)-(+)-propylene oxide and 2-methyl piperidine instead of (R)-2-methyl piperidine were used as reaction materials.

Example 5: Synthesis of CG-618

CG-618 (1-(1-(2-benzylphenoxy)propan-2-yl)-2-methylpiperidine) was synthesized in the same manner as the following Reaction Formula 2:

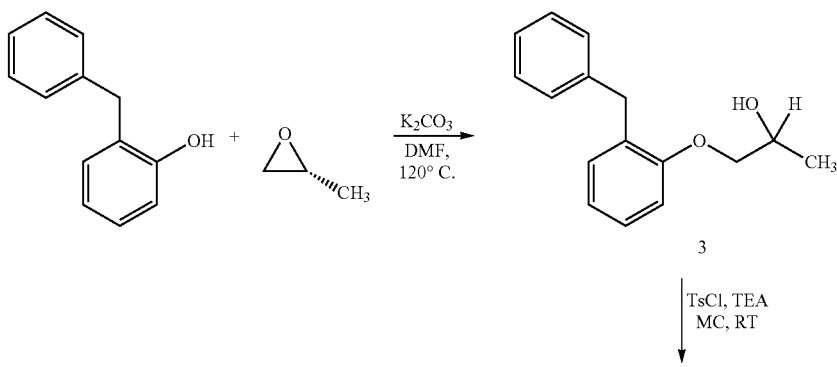

[Reaction Formula 2]

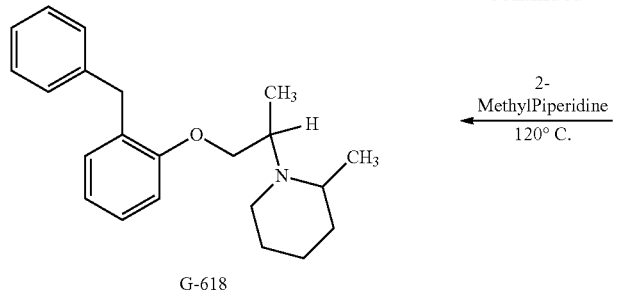

CG-618

CG-618 (1-(1-(2-benzylphenoxy)propan-2-yl)-2-methylpiperidine) was synthesized in the same manner as the synthesis method of CG-609, and there was a difference in that racemates of both propylene oxide and 2-methyl piperidine instead of enantiomers thereof were used as reaction materials.

Comparative Example 1: Synthesis of CG-605S

CG-605S was synthesized in the same manner as the synthesis method of CG-609, and there was a difference in that morpholine instead of 2-methyl piperidine was used as a reaction material.
The $^1$H-NMR analysis result of CG-605S is as follows:
$^1$H-NMR (300 MHz) δ 7.27-7.08 (m, 7H), 6.88 (m, 2H), 4.05 (dd, 1H, J=9.5, 5.1 Hz), 4.98 (s, 2H), 3.88 (dd, 1H, J=9.0, 5.5 Hz), 3.66 (t, 4H, J=4.5 Hz), 2.92 (m, 1H), 2.58 (m, 414), 1.12 (d, 311. J=7.2 Hz).

Comparative Example 2: Synthesis of CG-606S

CG-606S was synthesized in the same manner as the synthesis method of CG-609, and there was a difference in that pyrrolidine instead of 2-methyl piperidine was used as a reaction material.
The $^1$H-NMR analysis result of CG-606S is as follows:
$^1$H-NMR (500 MHz) δ 7.27-7.08 (m, 7H), 6.88 (m, 2H), 4.13 (dd, 1H, J=9.5, 5.0 Hz), 4.01 (s, 2H), 3.82 (dd, 1H, J=9.0, 7.0 Hz), 2.75 (m, 1H), 2.67 (m, 4H), 1.78 (m, 4H), 1.22 (d, 3H, J=6.5 Hz).

Comparative Example 3: Synthesis of CG-607S

CG-607S was synthesized in the same manner as the synthesis method of CG-609, and there was a difference in that hexamethyleneimine instead of 2-methyl piperidine was used as a reaction material.
The $^1$H-NMR analysis result of CG-607S is as follows:
$^1$H-NMR (500 MHz) δ 7.28-7.08 (m, 7H), 6.88 (m, 2H), 4.05 (dd, 1H, J=9.0, 5.0 Hz), 4.01 (s, 2H), 3.80 (dd, 1H, J=9.0, 7.0 Hz), 3.13 (m, 1H), 2.71 (m, 4H), 1.59 (m, 8H), 1.11 (d, 3H, J=7.0 Hz).

Comparative Example 4: Synthesis of CG-611

CG-611 was synthesized in the same manner as the synthesis method of CG-609, and there was a difference in that 3-methyl piperidine instead of 2-methyl piperidine was used as a reaction material.
The $^1$H-NMR analysis result of CG-611 is as follows:
$^1$H-NMR (500 MHz) δ 7.28-7.15 (m, 6H), 7.09 (m, 1H), 6.88 (m, 2H), 4.08 (m, 1H), 4.01 (s, 2H), 3.87 (m, 1H), 3.01 (m, 1H), 2.78 (m, 2H), 2.22 (m, 1H), 1.62 (m, 4H), 1.12 (dd, 3H, J=2.0, 7.0 Hz), 0.086 (dd, 3H, J=5.5, 7.0 Hz).

Comparative Example 5: Synthesis of CG-612

CG-612 was synthesized in the same manner as the synthesis method of CG-609, and there was a difference in that 3-methyl piperidine instead of 2-methyl piperidine was used as a reaction material.
The $^1$H-NMR analysis result of CG-612 is as follows:
$^1$H-NMR (500 MHz) δ 7.29-7.17 (m, 6H), 7.11 (m, 1H), 6.88 (m, 2H), 4.05 (dd, 1H, J=9.5, 5.0 Hz), 4.02 (s, 2H), 3.87 (dd, 1H, J=9.0, 6.5 Hz), 3.01 (m, 1H), 2.85 (m, 2H), 2.31 (m, 2H), 1.63 (m, 2H), 1.31 (m, 1H), 1.23 (m, 2H), 1.14 (d, 3H, J=7.0 Hz), 0.94 (d, 3H, J=6.5).

Experimental Example 1: Cytotoxicity Analysis

Figure 2:
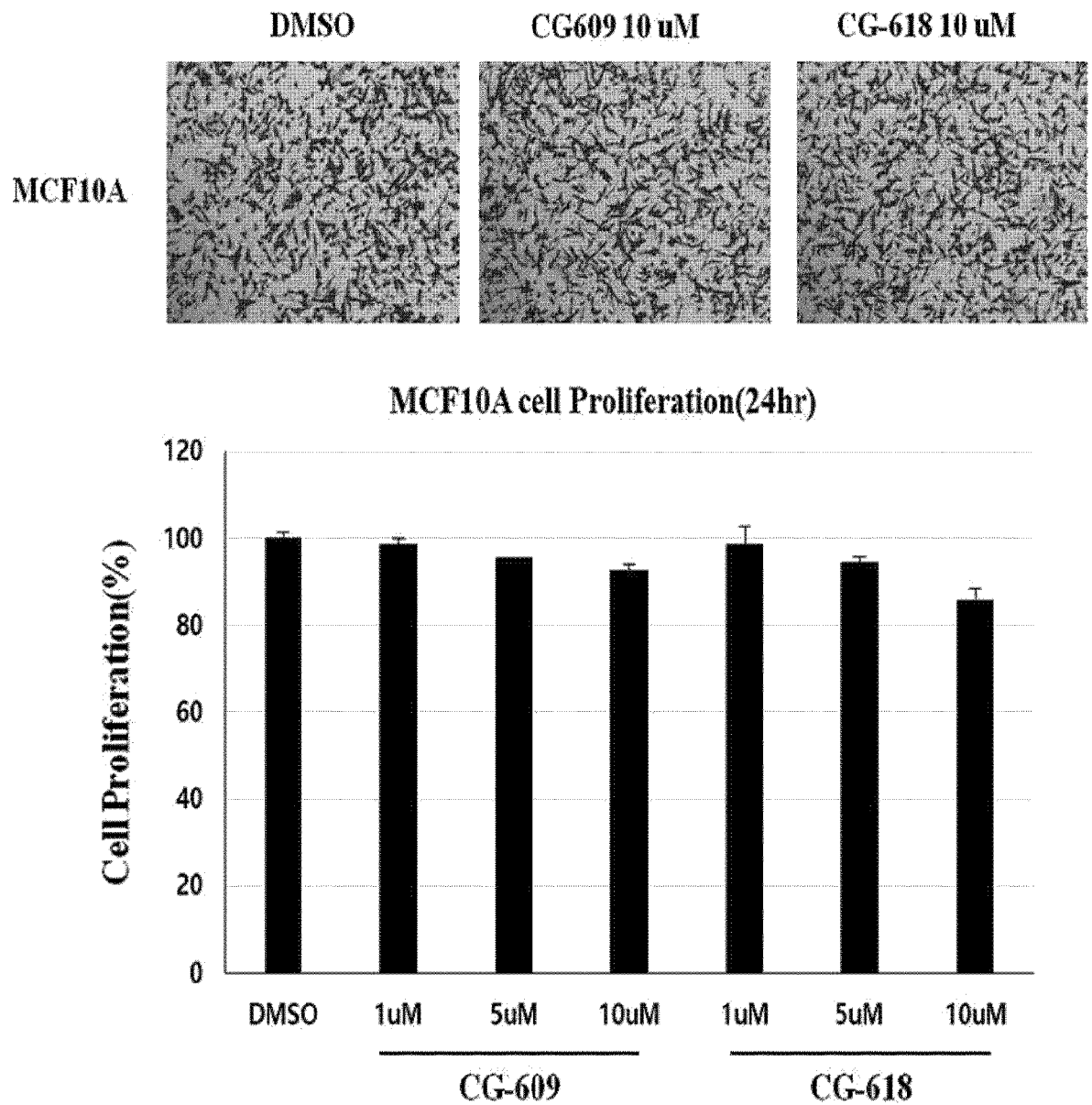
FIG. 2 is a diagram illustrating an effect of CG-609 and CG-618 on migration and proliferation of normal cells MCF-10A.

In order to verify cytotoxicity of CG-608 to CG-610 and CG-613 to CG-618 prepared in Examples 1 to 9, human colon cancer cell line DLD-1 cells (ATCC-CCL-221), pancreatic cancer cell line AsPc-1 cells (ATCC-CRL-1682), and normal cells MCF10A (ATCC-CRL-10317) were cultured in an RPMI medium containing 10% bovine fetal serum (FBS) while maintaining 37° C. and 5% $CO_2$, and then the cells were detached using a 0.05% trypsin-EDTA. 4×10$^3$ cells calculated by a hematocytometer were inoculated in each well of a 96-well plate containing a 10% FBS containing medium and cultured in a 37° C. incubator containing 5% $C_2$.
After 24 hours, the medium of each well was exchanged to a new medium containing a control group (0.1% DMSO) and CG-609 prepared in Example 1 or CG-618 prepared in Example 9 as a representative benproperine derivative at concentrations of 1 μM, 5 μM, and 10 μM. Thereafter, the cells were cultured in an incubator at 37° C. and 5% CO2 for 48 hours. Thereafter, 10 ml of WST-1 (Roche) was added to each well and cultured for 2 hours, and then the absorbance was measured at 450 nm using an ELISA reader (Bio-Rad).
As a result, as illustrated in FIG. 2, CG-609 and CG-618 did not exhibit cytotoxicity even in normal cells MCF10A.

Experimental Example 2: Analysis of Cancer Cell Migration Inhibitory Activity

In order to analyze cancer cell migration inhibitory activity of CG-608, CG-609 or CG-618 prepared in Examples 1, 2, or 9, cell migration inhibitory activity was measured using a trans-well by targeting a colon cancer cell line DLD-1 (ATCC-CCL-221), pancreatic cancer cell lines AsPc-1 (ATCC-CCL-1682). CFPAC-1 (ATCC-CCL-1918). Panc-1 (ATCC-CCL-1469), and Miapaca-2 (ATCC-CCL-1420), a skin cancer cell line A375-P (ATCC-CCL-3224), lung cancer cell lines HCC-827 (ATCC-CCL-2868), A549 (ATCC-CCL-185), and NCI-H460 (ATCC-CCL-177), a prostate cancer cell line DU145 (ATCC-HTB-81), a stomach cancer cell line NuGC-3 (JCRB0822), and an ovarian cancer cell line SKOV-3 (ATCC-HTB-77).

First, the number of DLD-1 cells was measured using a hemocytometer in an RPMI medium without FBS. Thereafter, the trans-well was placed on a 24-well plate and $8\times10^4$ cells/200 mL of cells were added. In an empty space with the trans-well on the well plate, 500 mL of an RPM medium having 10% FBS containing CG-608, CG-609, or CG-618 was added and cultured in a $CO_2$ incubator at 37° C. for 16 hours. After culture, 500 mL of crystal violet (5 mg/mL of 20% Me(H) was added to each well of the 24-well plate and the trans-well was dyed at room temperature for 30 minutes. The dyed trans-well was washed with PBS and non-migrated cells were wiped off with cotton swabs. The prepared sample was photographed with an inverted microscope mounted with a digital camera (TE 300, Nikon. Japan) and then the number of migrated cells was counted. The degree of inhibiting cell migration was calculated by Equation 1 for a group treated with the sample compared to a control group (DMSO).

$$\text{Degree of inhibiting cell migration}(\%) = 100 - \left[\frac{\text{the number of migrated cells treated with sample}}{\text{the number of migrated cells of control sample}} \times 100\right] \quad \text{[Equation 1]}$$

In Equation 1, 'the number of migrated cells treated with sample' refers to the number of migrated cells measured by treating CG-608 or CG-618 of Example 1, and 'the number of migrated cells of a control sample' refers to the number of migrated cells measured by treating only 1% dimethyl sulfoxide (DMSO) instead of the compound.

Figure 3:
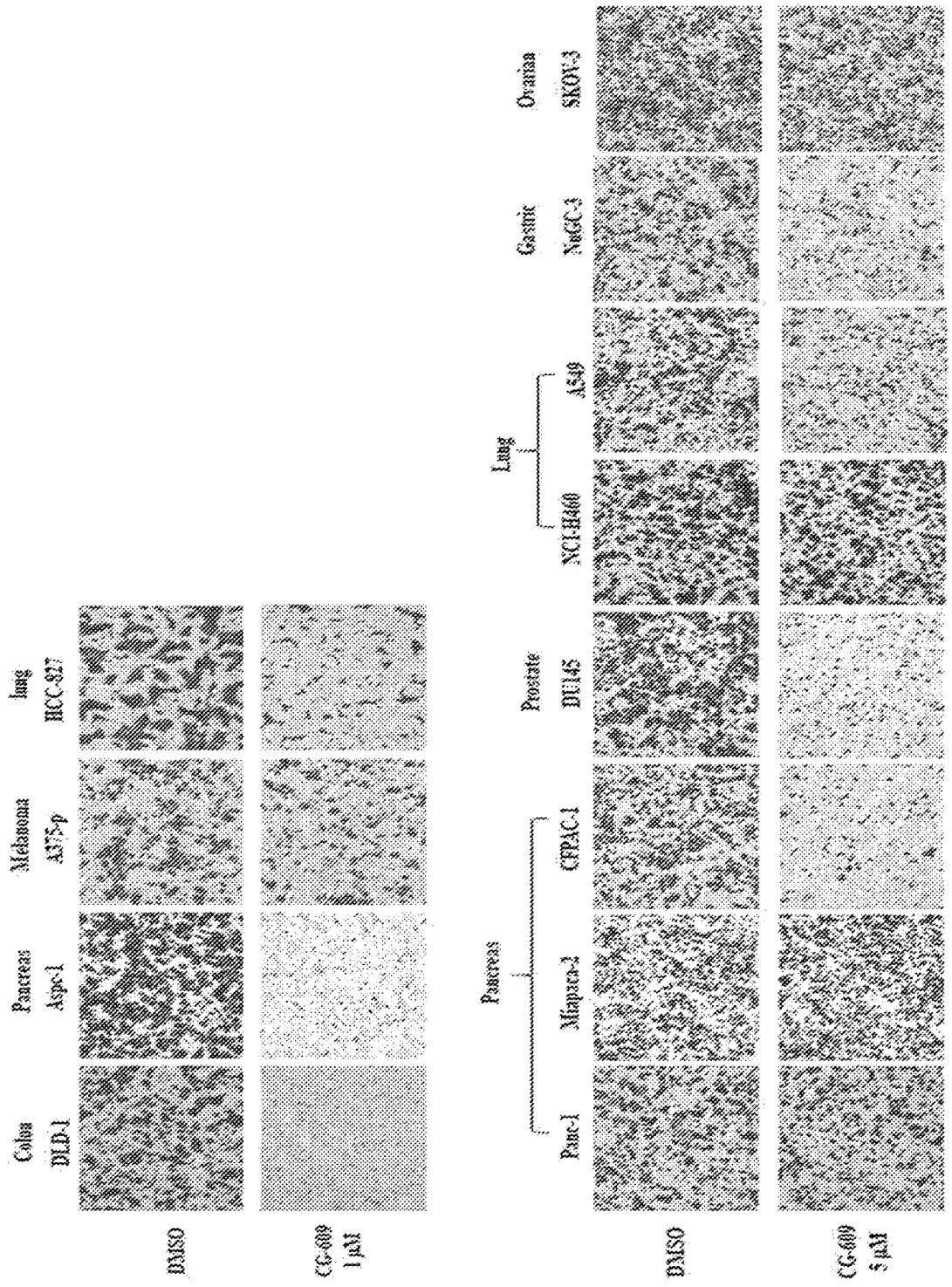
FIG. 3 is a diagram illustrating measurement of cancer cell migration inhibitory activity of CG-609 with respect to a colon cancer cell line DLD-1; pancreatic cancer lines AsPc-1, CFPAC-1, Panc-1, and Miapaca-2; a skin cancer cell line A375-P; lung cancer cell lines HCC-827. A549, and NCI-11460: a prostate cancer cell line DU145; a stomach cancer cell line NuGC-3; and an ovarian cancer cell line SKOV-3.

As a result, as illustrated in FIG. 3, it was confirmed that the migration of colon cancer cells DLD-1, a pancreatic cancer cell line AsPc-1, skin cancer cells A375-P. and lung cancer cells HCC-827 was inhibited by 50% or more by treating 1 µM of CG-609 and the migration of pancreatic cancer cells CFPAC-1, lung cancer cells A549, prostate cancer cells DU-145, and stomach cancer cells NuGC-3 was inhibited by 50% or more by treating CG-609.

Further, the concentration dependence of the compound on cancer cell migration was confirmed and the results were summarized in Table 1 and FIGS. 4A, 4B, 5, 6A, and 6B.

TABLE 1

Concentrations of inhibiting migration of cancer cells in CG-608, CG-609, CG-618 and benproperine by 50% ($IC_{50}$ value)

| Cancer cell | $IC_{50}$ of CG-608 | $IC_{50}$ of CG-609 | $IC_{50}$ of CG-618 | $IC_{50}$ of benproperine |
|---|---|---|---|---|
| Colon cancer cell DLD-1 | 200 nM | 60 nM | 550 nM | 2 µM |
| Pancreatic cancer cell line AsPc-1 | 250 nM | 110 nM | 700 nM | 3 µM |
| Skin cancer cell A375-P | 1.5 µM | 700 nM | 3 µM | 7 µM |
| Prostate cancer cell DU145 | 5 µM | 2 µM | 3 µM | 20 µM |
| Lung cancer cell HCC-827 | 1.5 µM | 210 nM | 500 nM | 20 µM |
| Gastric cancer cell NuGC-3 | 2.0 µM | 5 µM | 8 µM | <20 µM |

Meanwhile, as seen in FIG. 2, it was shown that CG-609 and CG-618 did not inhibit the cell migration and growth of normal cells MCF10A.

Figure 4A:
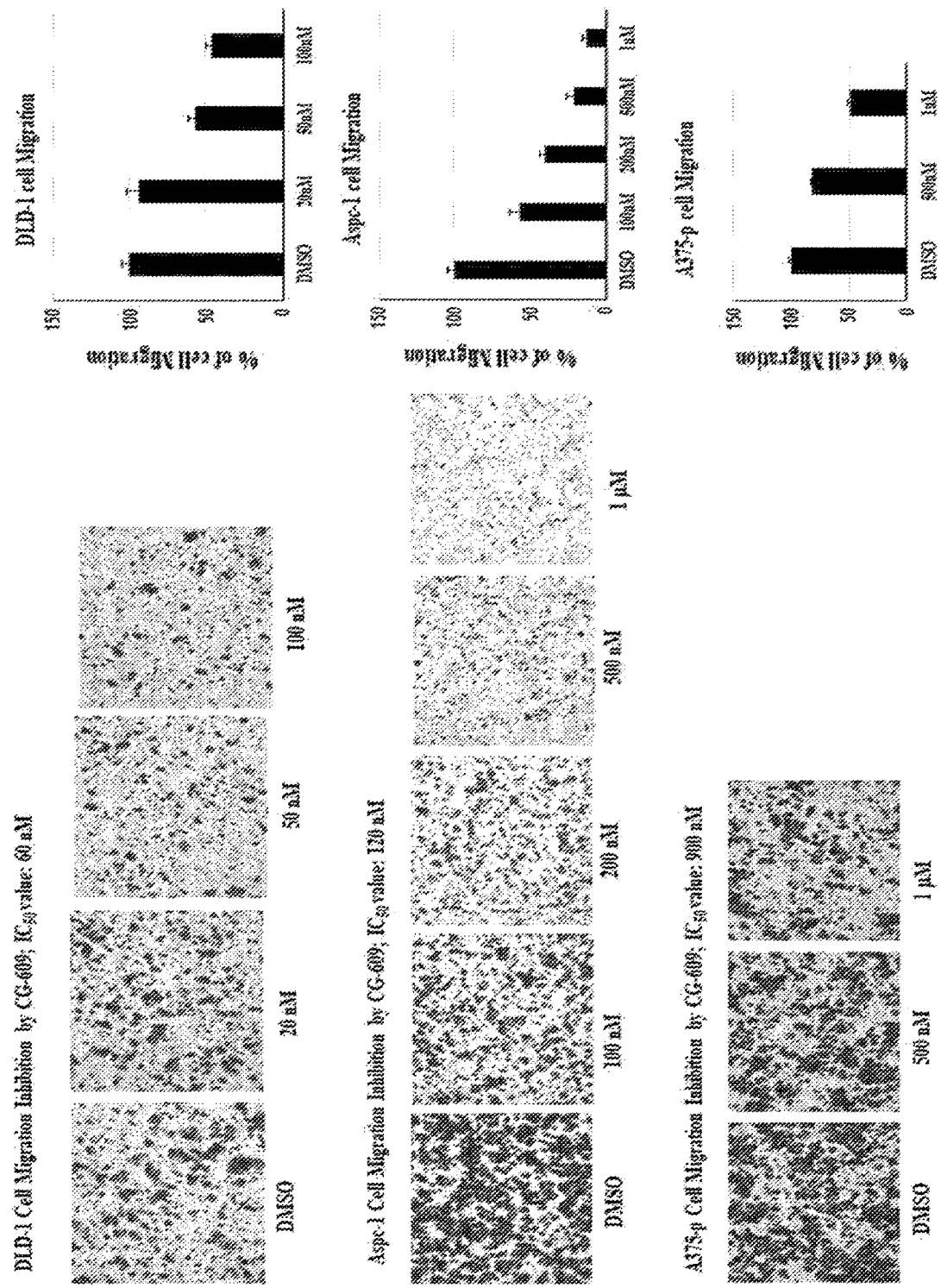
FIG. 4A is a diagram illustrating measurement of cancer cell migration inhibitory activity for each concentration of CG-609 with respect to a colon cancer cell line DLD-1, a pancreatic cancer line of AsPc-1, and a skin cancer cell line A375-P.
Figure 4B:
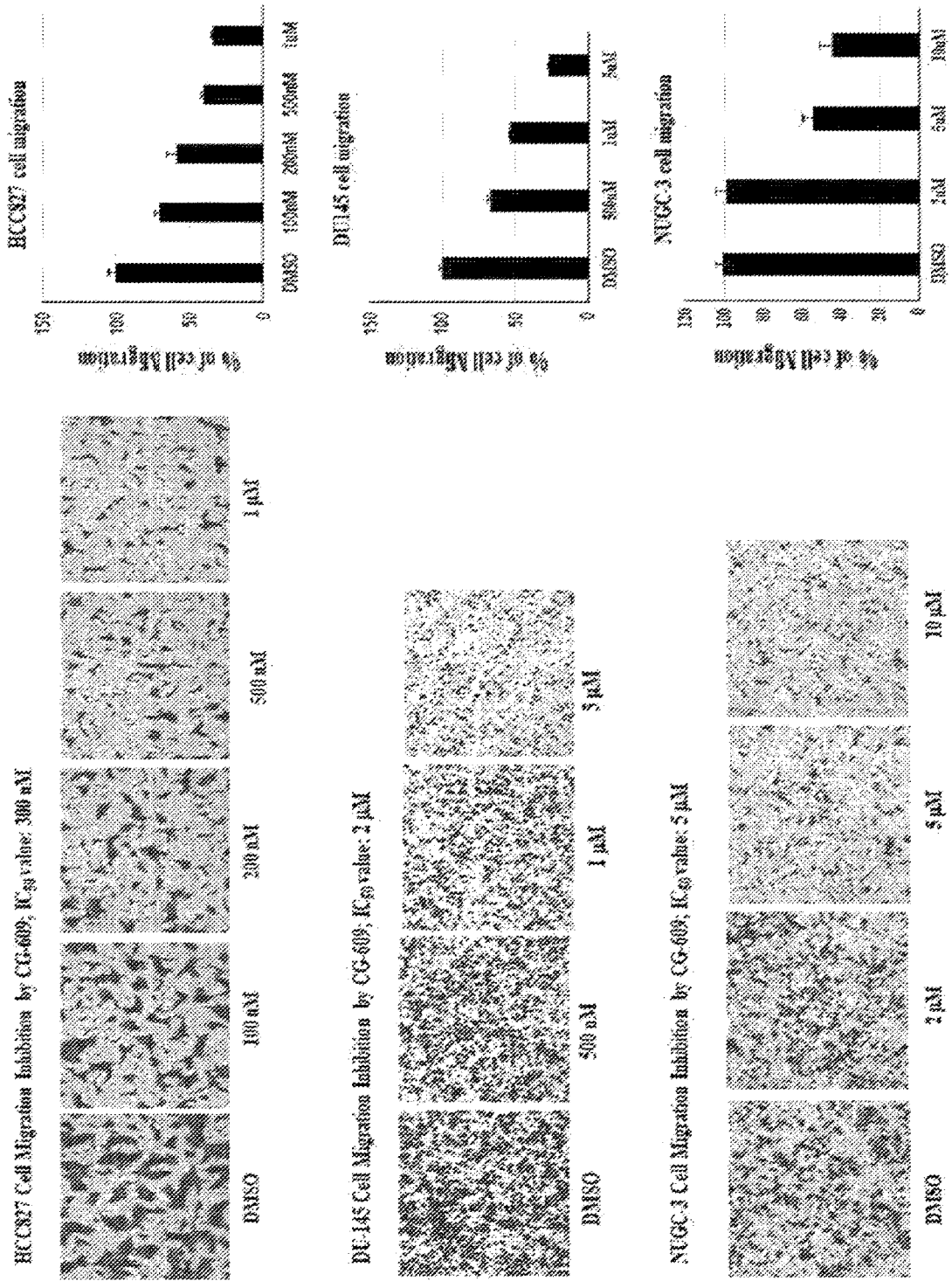
FIG. 4B is a diagram illustrating measurement of cancer cell migration inhibitory activity for each concentration of CG-609 with respect to a lung cancer cell line HCC827, a prostate cancer cell line DU145, and a stomach cancer cell line NuGC-3.
Figure 5:
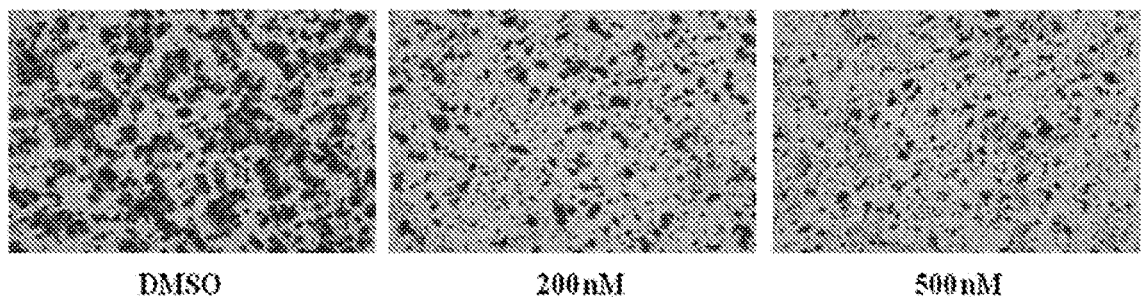
FIG. 5 is a diagram illustrating measurement of cancer cell migration inhibitory activity for each concentration of CG-608 with respect to a colon cancer cell line DLD-1, a pancreatic cancer line of AsPc-1, a prostate cancer cell line DU145, and a stomach cancer cell line NuGC-3.
Figure 5:
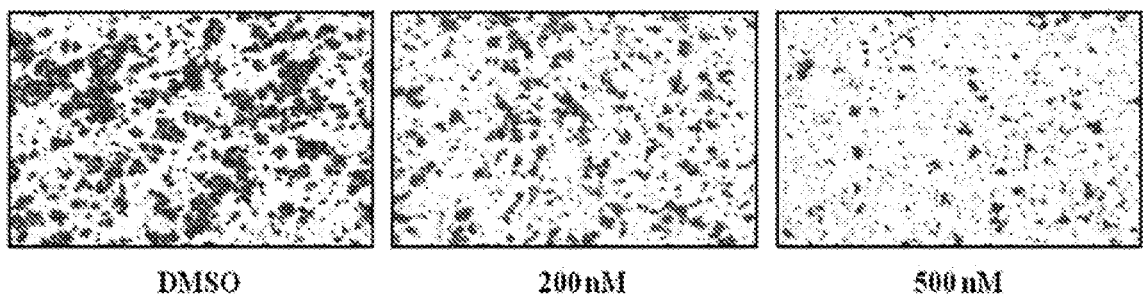
Figure 5:
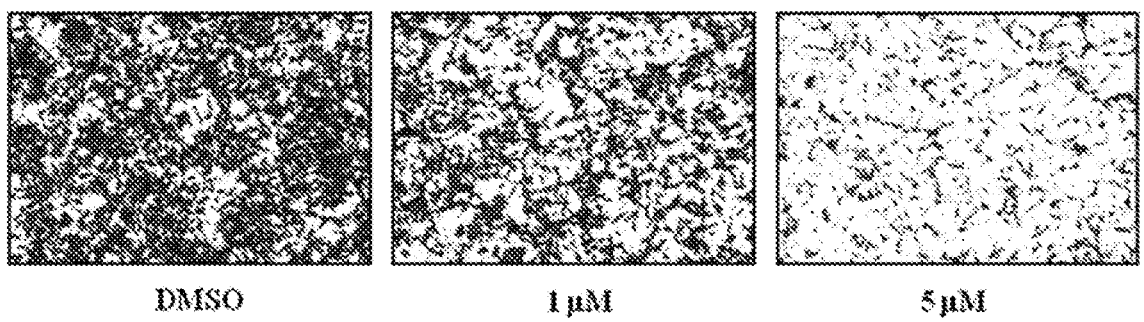
Figure 5:
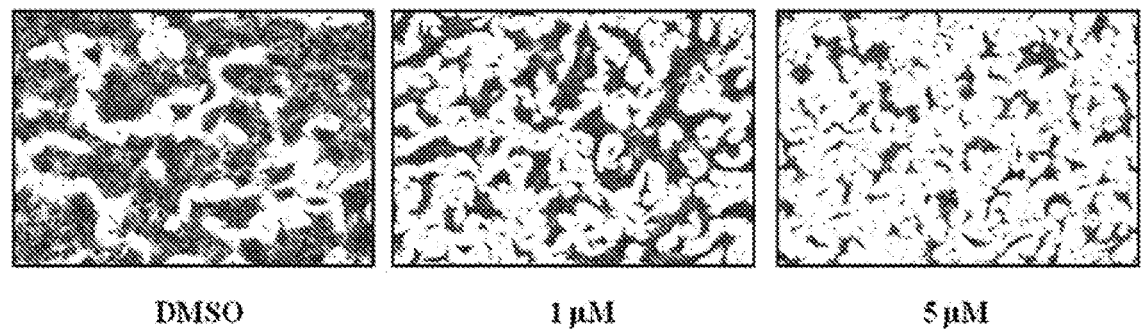
Figure 6A:
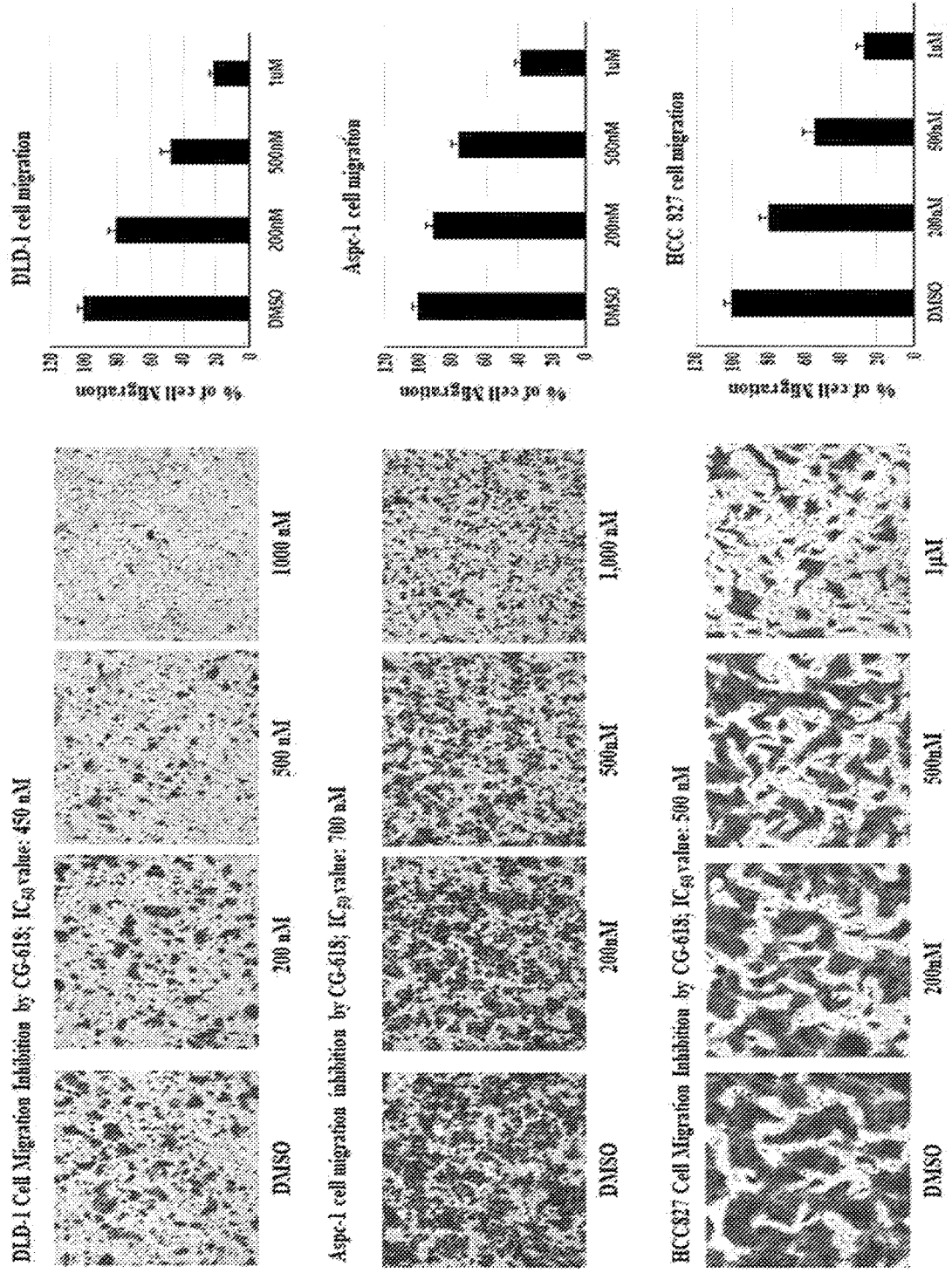
FIG. 6A is a diagram illustrating measurement of cancer cell migration inhibitory activity for each concentration of CG-618 with respect to a colon cancer cell line DLD-1, a pancreatic cancer line of AsPc-1, and a lung cancer cell line HCC827.
Figure 6B:
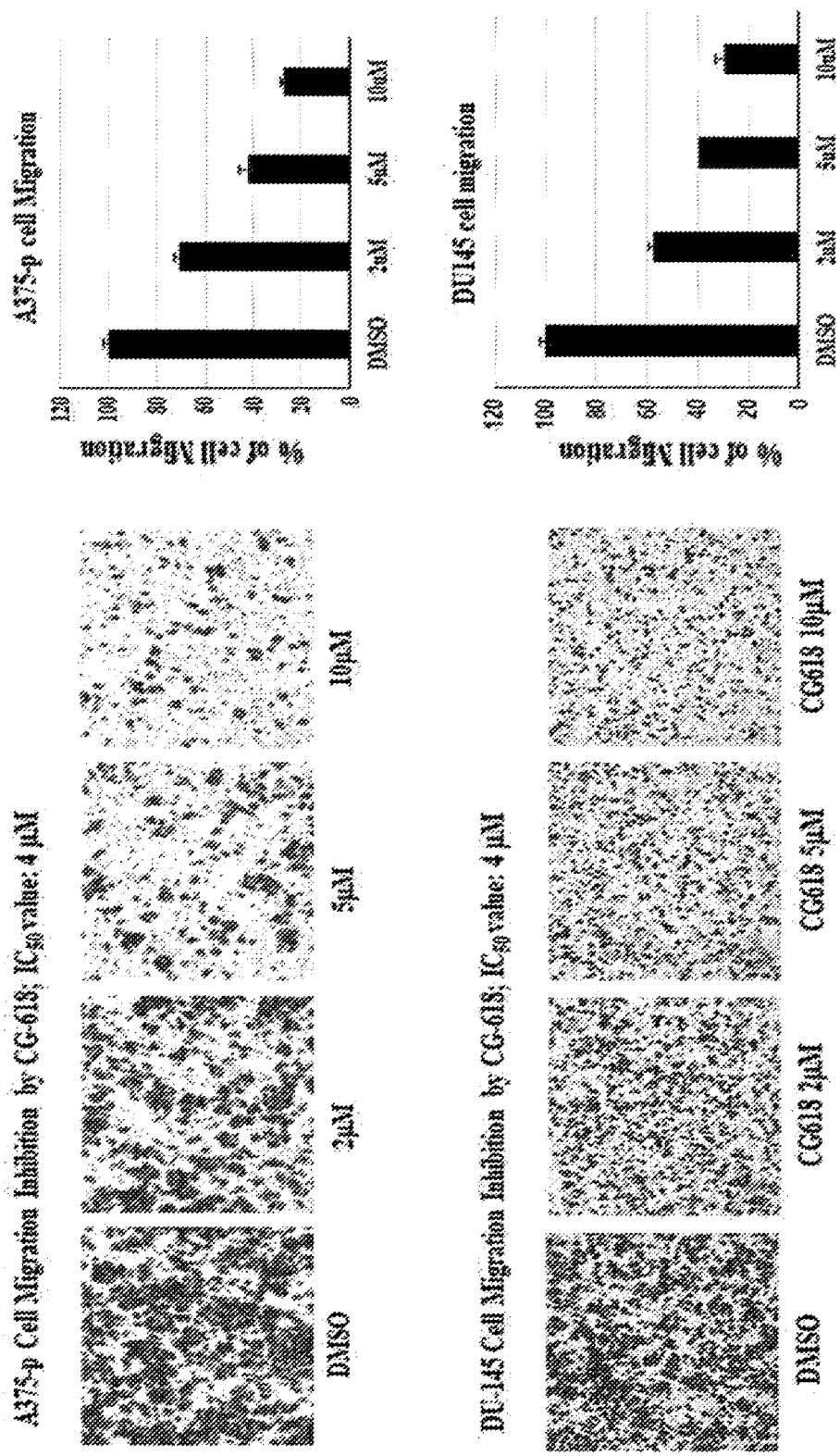
FIG. 6B is a diagram illustrating measurement of cancer cell migration inhibitory activity for each concentration of CG-618 with respect to a skin cancer cell line A375-p and a prostate cancer cell line DU145.

Further, as illustrated in FIG. 4A, in Korean Patent Publication No. 10-2016-0105744, it can be seen that a benproperine derivative compound needs to be treated at a concentration of as much as 2 µM to inhibit 50% or more of migration of cancer cells under the same condition, while CG-609 inhibits 50% or more of migration of DLD-1 cells even if being treated at a 50 nM concentration, which is significantly lower.

Accordingly, it can be seen that CG-609 has more than 20 times stronger cancer cell migration inhibitory activity than the benproperine derivative compound known in the related art.

Experimental Example 3: Analysis of Cancer Cell Invasion Inhibitory Activity

In order to analyze cancer cell invasion inhibitory activity of CG-609 or CG-618 prepared in Example 1 or 9, cell invasion inhibitory activity using a trans-well was measured by targeting colon cancer cell line DLD-1 cells or pancreatic cancer cell line AsPc-1 cells.

Matrigel was diluted by 1/5 using an RPMI medium without FBS and then 200 mL was put into each trans-well. The cells were coated in a CO incubator for 2 hours. The number of DLD-1 cells was measured using a hemocytometer in an RPMI medium without FBS. Thereafter, the coated trans-well was placed on a 24-well plate and $8\times10^4$ cells/200 mL of cells were added. In an empty space of the trans-well on the well plate, 500 mL of an RPMI medium having 10% FBS containing (S)-(−)-benproperine was added and cultured in a $CO_2$ incubator at 37° C. for 16 hours. After culture, 500 mL of crystal violet (5 mg/mL of 20% MeOH) was added to each well of the 24-well plate and the trans-well was dyed at room temperature for 30 minutes. The dyed trans-well was washed with PBS and non-migrated cells were wiped off with cotton swabs. The prepared sample was photographed with an inverted microscope mounted with a digital camera (TE 300, Nikon, Japan), and then the number of migrated cells was counted. The degree of inhibiting cell migration was calculated for a group treated with the sample compared to a control group (DMSO).

Figure 8:
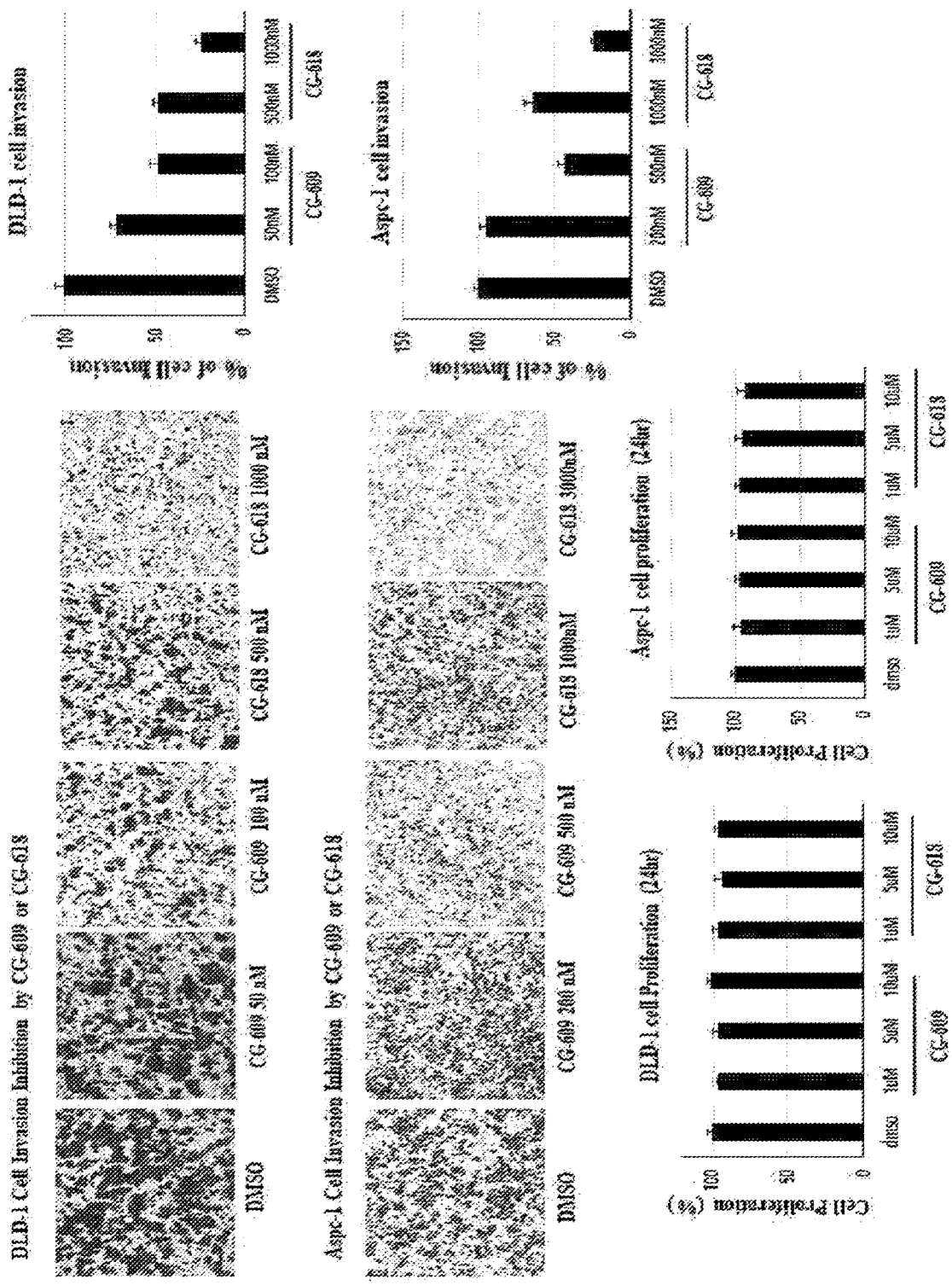
FIG. 8 is a diagram illustrating concentration-dependent cancer cell invasion and proliferation inhibitory effects of CG-609 and CG-618 for a colon cancer cell line DLD-1 and a pancreatic cancer line of AsPc-1.

As a result, as illustrated in FIG. 8, it was confirmed that CG-609 100 nM and CG-618 500 nM were treated in colon cancer cells DLD-1, respectively, to inhibit 50% or more of cell invasion as compared with a DMSO-treated control sample. When comparing a result of inhibiting 50% of cell invasion only when 5 µM of benproperine was treated, it can be seen that CG-609 and CG-618 strongly inhibited the cell invasion even at a very low concentration.

As described above, it was confirmed that CG-609 and CG-618 effectively inhibited invasion of cancer cells as well as migration of cancer cells. It is suggested that CG-609 and CG-618 or the composition containing the pharmaceutically acceptable salt thereof may be usefully used for preventing or treating various cancer metastases.

Experimental Example 4: Real-Time Cell Migration Imaging and Analysis

An effect of a drug on migration of single cells was confirmed using HoloMonitor M4 (Phase Holographic Imaging), real-time cell migration imaging and analysis equipment. All experiments were performed within a 37° C. cell incubator to analyze cell migration while cells were alive for a long time. To prevent water vapor generated during cell imaging for a long time from obstructing the imaging, the experiment was conducted by dividing cells in an m-slide microcopy chamber (Ibidi). In order to analyze migration of single cells, cells ($2.5 \times 10^5$ cells/mL) to be analyzed were divided to the m-slide microscopy chamber by 0.2 mL and cultured for more than 12 hours. The cells were sufficiently attached to its original shape and then treated with the drug, and a position to be analyzed was specified, and then the cell migration was measured in real time.

Figure 7:
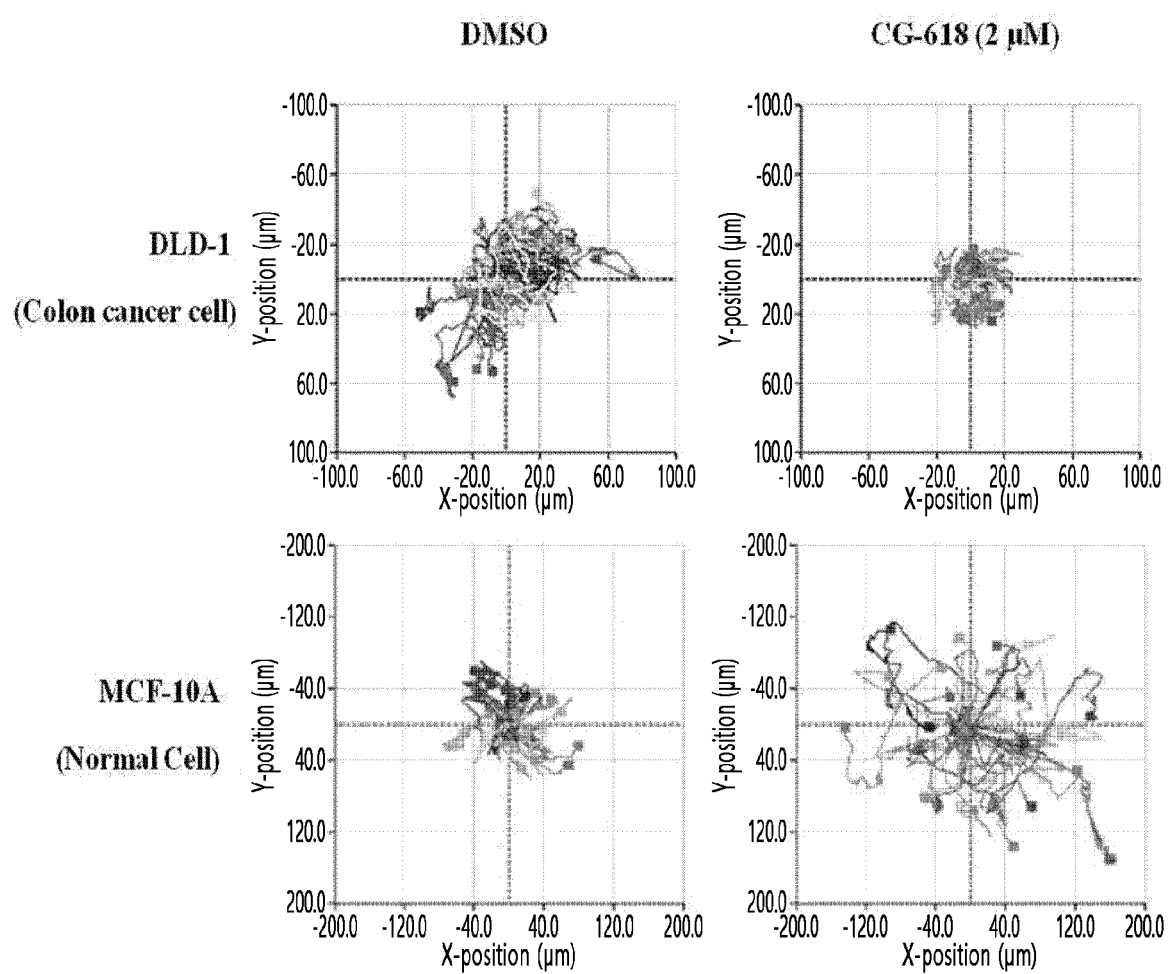
FIG. 7 is a diagram illustrating an effect of CG-618 on migration of a colon cancer cell line DLD-1 and a normal cell line MCF-10A.

The cell migration was measured for 24 hours at five-minute intervals, and migration of 25 cells per group was analyzed. Using the HoloMonitor tracking software, a total distance migrated by the cells during the time measured, a linear distance from the starting point to the arrival point, a rate of migration, and a direction were quantitatively analyzed, and the migration of single cells was visualized with a Wind-Rose plot (FIG. 7).

Figure 9:
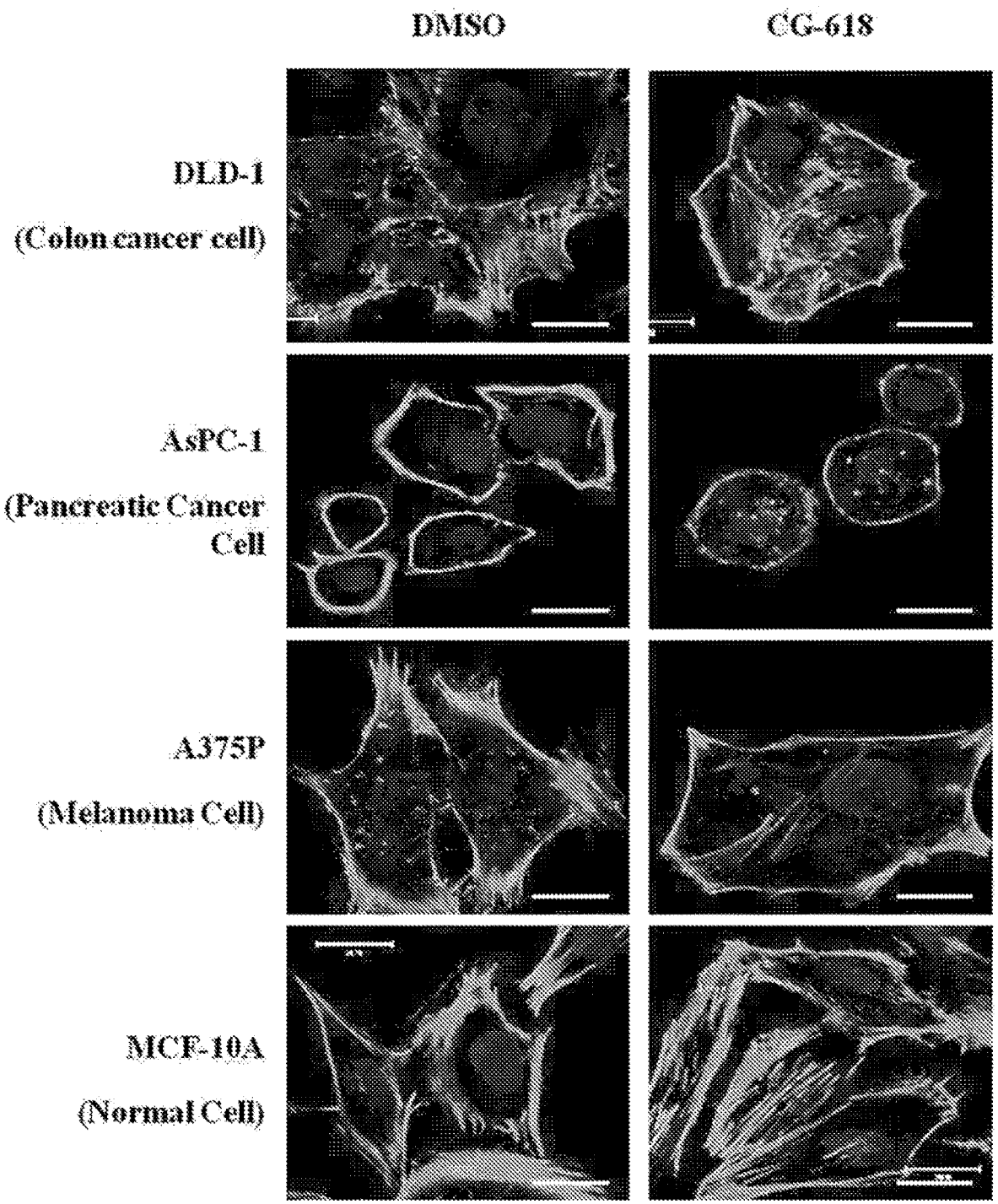
FIG. 9 is a diagram illustrating that CG-618 inhibits formation of lamellipodia of a colon cancer cell line DD-1, a pancreatic cancer line of AsPc-1, and a skin cancer cell line A375-p, but has no effect on a normal cell line MCF-10A.

Experimental Example 5: Measurement of Lamellipodia Formation Inhibitory Activity Using Confocal Microscope A human colon cancer cell line DLD-1, a human pancreatic cancer cell line AsPc-1, a human melanoma cell line A375P, and normal cells MCF10A were each cultured to $1 \times 10^5$ cell density on a 35 mm high-m dish plate (ibid GmbH). The cells attached to the plate were washed with phosphate buffered saline (PBS) and then treated with DMSO or CG-618 dissolved in DMSO for 6 hours. After removing the cell culture medium from the plate, the plate was washed two times with PBS and treated with 4% paraformaldehyde dissolved in PBS at room temperature for 10 minutes to immobilize the cells. The plate was washed with PBS once and then treated with 0.2% Triton X-100 at room temperature for 10 minutes to enhance cell permeability. The plate was washed with PBS and treated with 1% BSA dissolved in PBS at room temperature for 1 hour to block non-specific bonds. In order to check the distribution in cells of filament actin (F-actin), phalloidin bound with Alexa Fluor 488, which was specifically bound with F-actin, was treated at room temperature for 15 minutes. The plate was washed with PBS three times and then treated with 2 mg/mL 4',6'-diamidino-2-phenylindole (DAPAI) dissolved in PBS for two minutes at room temperature to dye the nucleus. The plate was washed with PBS three times and filled with 1 mL PBS. Images of dyed cells were obtained using a confocal microscope (LSM 510 META, Carl Zeiss Vision) and illustrated in FIG. 9. The obtained images were analyzed by an analysis program (LSM Version 3.2 software).

Experimental Example 6: Acute Toxicity Test for Oral Administration to Rats

Six-week-old specific pathogen free (SPF) SD-based rats were divided by two per group and then CG-608, CG-609, or CG-618 prepared in Example 1, 2, or 9 was dissolved in distilled water for injection and orally administered to rats once in a dose of 1000 mg/kg. After administering a test substance, animal mortality, clinical symptoms, and weight changes were observed, a hematological test and a blood biochemical test were conducted, and after an autopsy, abnormalities in abdominal and chest organs were observed with the naked eye.

As a result, there were no special clinical symptoms or dead animals in all animals administered with the test substance, and toxic changes were not observed in weight changes, hematological and blood biochemical tests, autopsy findings, etc.

Therefore, since CG-608, CG-609, and CG-618 did not exhibit toxic changes up to 1000 mg/kg in all rats, the minimum dose ($LD_{50}$) of oral administration was determined to be a safe substance of 1000 mg/kg or more.

Experimental Example 7: Verification of Cancer Metastasis Inhibitory Activity of CG-609 in Liver Metastasis Model Using Nude Mouse In this experiment, a human-derived colon cancer cell line (HCT-116 luciferase) was implanted to the spleen and then the spleen was removed and sutured after four days. In a colon cancer liver metastasis implant model, cancer metastasis inhibitory activity by oral administration of CG-609 was verified using a live animal imaging system. As the animal, an Athymic-NCr NCr-nu SPF 5-week-old nude mouse supplied from Koatech (Pyeongtaek-si, Gyeonggi-do) was used. By adjusting a concentration of cancer cells to $2 \times 10^6$ cells/mL, the cell culture solution was injected directly into the spleen using a syringe (31 G needle, ½ cc) by 30 μL per mouse. The drug CG-609 was dissolved to a concentration of 5 mg/kg or 10 mg/kg using 0.5% Tween80 and then orally administered to the mouse in an amount of 10 mL/kg total 20 times on a schedule of five times a week.

Figure 10A:
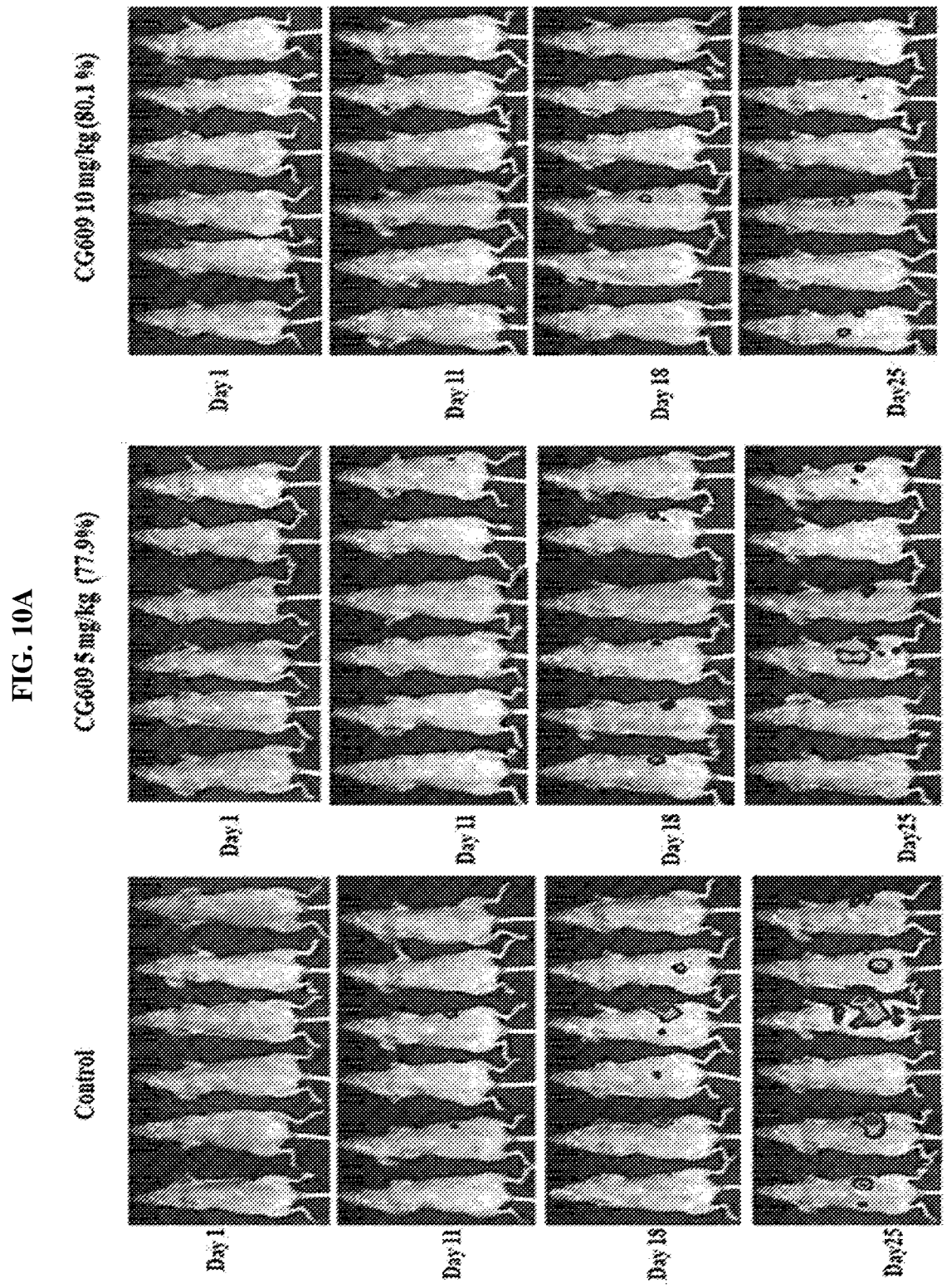
FIGS. 10A and 10B are diagrams illustrating results of confirming cancer metastasis inhibitory activity by oral administration (dose of 5 mg/kg and 10 mg/kg) in a colon cancer liver metastasis implant model in a live animal imaging system.
Figure 10B:
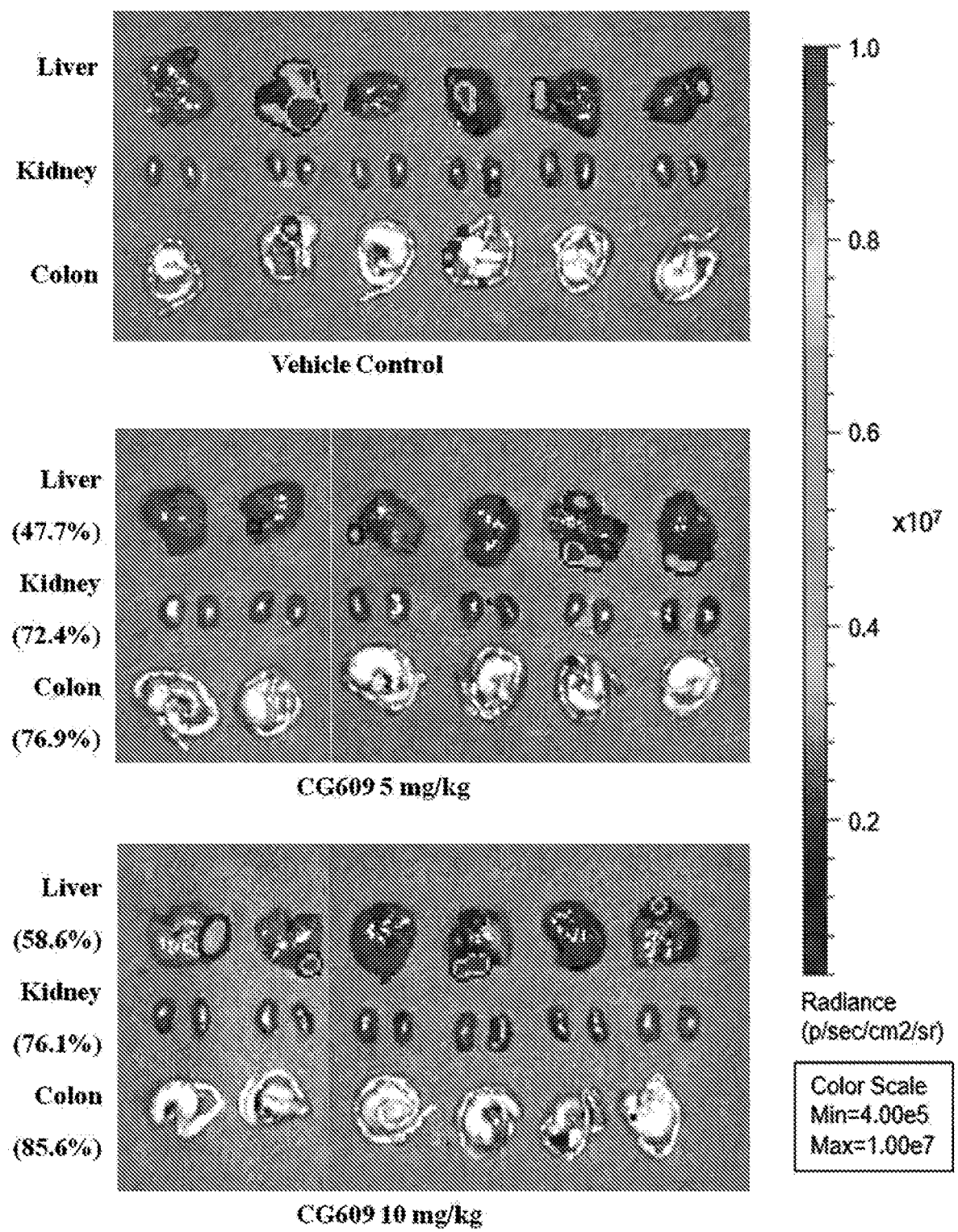
Figure 11:
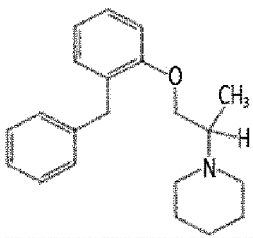
FIG. 11 is a diagram illustrating $IC_{50}$ values for migration of a colon cancer cell line DLD-1 in benproperine as a control, and Structural Formulas of compounds of Examples 1 to 3 and 5 and compounds thereof.
Figure 11:
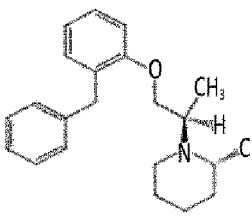
Figure 11:
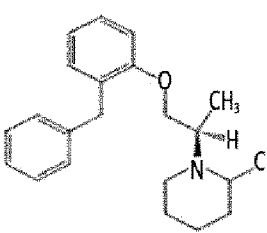
Figure 11:
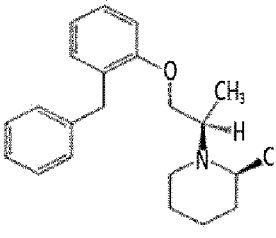
Figure 11:
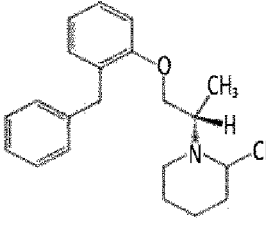
Figure 11:
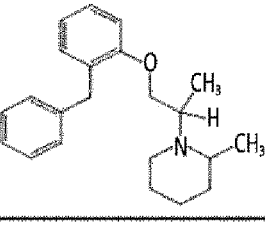

HCT-116 luciferase cells were implanted, drug administration started from the day after the cancer cell was implanted, and the cells were imaged a total of seven times until the 25th day, the end of the experiment. During imaging, 50 μL of cells was intraperitoneally administered into each side of the animal's abdomen at a concentration of luciferin 15 mg/mL, and then photographed using an optical imaging system (IVIS-spectrum CT, PerkinElmer). On the final day of the test, the mouse was imaged and then dyed, and major organs (liver, kidney, and colon) were extracted to be imaged, and then the degree of image signal was measured. The values of all measurement items were tested for statistical significance by comparing a solvent control and a drug administration group using a t-TEST statistical method (FIGS. 10A and 10B). Cancer metastasis inhibitory activity was summarized in Table 2.

TABLE 2

Cancer metastasis inhibitory activity in animal model of CG-609

|  | 5 mg/kg (%) | 10 mg/kg (%) |
| --- | --- | --- |
| Cancer metastasis inhibitory effect by whole image data | 77.9 | 80.1 |
| Liver metastasis inhibitory effect | 47.7 | 58.6 |
| Renal metastasis inhibitory effect | 72.4 | 76.1 |
| Colon metastasis inhibitory effect | 76.9 | 85.6 |

As described above, it was confirmed that CG-609 inhibited the migration and invasion of cancer cells and effectively inhibited cancer metastasis in an animal model. It is suggested that a composition containing CG-609 or a pharmaceutically acceptable salt thereof may be usefully used for preventing or treating various cancer metastases.

It will be appreciated by those skilled in the art that the present invention as described above may be implemented in other specific forms without departing from the technical spirit thereof or essential characteristics. Thus, it is to be appreciated that embodiments described above are intended to be illustrative in every sense, and not restrictive. The scope of the present invention is represented by the claims to be described below rather than the detailed description, and it is to be interpreted that the meaning and scope of the claims and all changes or modified forms derived from the equivalents thereof come within the scope of the present invention.

The invention claimed is:

1. A compound having a structure of the following Chemical Formula 1 or a pharmaceutically acceptable salt thereof, as a benproperine derivative compound:

[Chemical Formula 1]

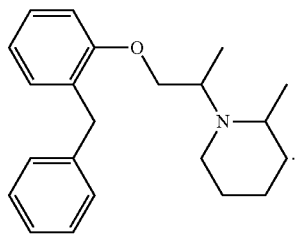

2. A pharmaceutical composition for preventing or treating cancer metastasis, containing the compound of claim 1 or a pharmaceutically acceptable salt thereof as an active ingredient wherein the cancer is any one selected from the group consisting of colon cancer, pancreatic cancer, stomach cancer, liver cancer, breast cancer, cervical cancer, thyroid cancer, parathyroid cancer, lung cancer, prostate cancer, gallbladder cancer, biliary tract cancer, non-Hodgkin's lymphoma, Hodgkin's lymphoma, blood cancer, bladder cancer, kidney cancer, ovarian cancer, melanoma, colon cancer, bone cancer, skin cancer, head cancer, uterine cancer, rectal cancer, brain tumor, anal cancer, paraplegic cancer, endometrial cancer, vaginal cancer, mucinoma, esophageal cancer, small intestine cancer, endocrine gland cancer, adrenal cancer, soft tissue sarcoma, urethral cancer, penis cancer, ureteric cancer, kidney cell carcinoma, kidney pelvic cancer, CNS (central nervous system) tumor, primary CNS lymphoma, spinal cord tumor, brainstem glioma, and pituitary adenoma.

3. The pharmaceutical composition for preventing or treating cancer metastasis of claim 2, wherein the composition further includes a pharmaceutically acceptable carrier, excipient, or diluent.

4. The pharmaceutical composition for preventing or treating cancer metastasis of claim 2, wherein the composition further includes an anti-cancer agent.

5. The pharmaceutical composition for preventing or treating cancer metastasis of claim 4, wherein the anti-cancer agent is at least one selected from the group consisting of DNA alkylating agents, anti-cancer antibiotics, and plant alkaloids.

6. The pharmaceutical composition for preventing or treating cancer metastasis of claim 4, wherein the anti-cancer agent is at least one selected from the group consisting of mechloethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin, C-bleomycin; vincristine, vinblastine, paclitaxel, docetaxel, etoposide, teniposide, topotecan, and iridotecan.

7. A health functional food for preventing or improving cancer metastasis, containing the compound of claim 1 or a sitologically acceptable salt thereof as an active ingredient.

8. A method for preventing or treating cancer metastasis, comprising administering, to a subject, a pharmaceutical composition containing the compound of claim 1 or a pharmaceutically acceptable salt thereof as an active ingredient, wherein the cancer is any one selected from the group consisting of colon cancer, pancreatic cancer, stomach cancer, liver cancer, breast cancer, cervical cancer, thyroid cancer, parathyroid cancer, lung cancer, prostate cancer, gallbladder cancer, biliary tract cancer, non-Hodgkin's lymphoma, Hodgkin's lymphoma, blood cancer, bladder cancer, kidney cancer, ovarian cancer, melanoma, colon cancer, bone cancer, skin cancer, head cancer, uterine cancer, rectal cancer, brain tumor, anal cancer, paraplegic cancer, endometrial cancer, vaginal cancer, mucinoma, esophageal cancer, small intestine cancer, endocrine gland cancer, adrenal cancer, soft tissue sarcoma, urethral cancer, penis cancer, ureteric cancer, kidney cell carcinoma, kidney pelvic cancer, CNS (central nervous system) tumor, primary CNS lymphoma, spinal cord tumor, brainstem glioma, and pituitary adenoma.

* * * * *